(12) United States Patent
Kressy et al.

(10) Patent No.: US 7,787,936 B2
(45) Date of Patent: Aug. 31, 2010

(54) METHODS AND APPARATUS FOR PERFORMING PROCEDURES ON TARGET LOCATIONS IN THE BODY

(75) Inventors: Matthew S. Kressy, Wellesley, MA (US); Leslie Greengard, New York, NY (US); Zachary S. Spigelman, Newton, MA (US); Richard H. Theriault, Lincoln, MA (US); Shekhar G. Wadekar, Westwood, MA (US); Steven B. Woolfson, Boston, MA (US)

(73) Assignee: Traxyz Medical, Inc., Needham, MA (US)

( * ) Notice: Subject to any disclaimer, the term of this patent is extended or adjusted under 35 U.S.C. 154(b) by 1621 days.

(21) Appl. No.: 11/041,347

(22) Filed: Jan. 24, 2005

(65) Prior Publication Data
US 2005/0165299 A1 Jul. 28, 2005

Related U.S. Application Data

(60) Provisional application No. 60/539,023, filed on Jan. 23, 2004.

(51) Int. Cl.
*A61B 5/05* (2006.01)
(52) U.S. Cl. .................... 600/427; 600/407
(58) Field of Classification Search ............ 600/407, 600/410, 411, 415, 417, 424, 427, 429, 439, 600/562; 378/37; 606/130
See application file for complete search history.

(56) References Cited

U.S. PATENT DOCUMENTS

| | | | | |
|---|---|---|---|---|
| 4,911,173 A | * | 3/1990 | Terwilliger | 600/464 |
| 5,042,486 A | | 8/1991 | Pfeiler et al. | |
| 5,115,816 A | * | 5/1992 | Lee | 600/562 |
| 5,211,165 A | | 5/1993 | Dumoulin et al. | |
| 5,279,309 A | * | 1/1994 | Taylor et al. | 600/595 |
| 5,377,678 A | | 1/1995 | Dumoulin et al. | |
| 5,386,447 A | * | 1/1995 | Siczek | 378/37 |
| 5,415,169 A | | 5/1995 | Siczek et al. | |

(Continued)

FOREIGN PATENT DOCUMENTS

DE 2139433 2/1973

(Continued)

OTHER PUBLICATIONS

International Search Report for PCT/US2005/002099 mailed May 24, 2005.

*Primary Examiner*—Long V Le
*Assistant Examiner*—Nicholas L Evoy
(74) *Attorney, Agent, or Firm*—Lando & Anastasi, LLP

(57) ABSTRACT

A method of performing a medical procedure on target tissue within the body includes immobilizing the target tissue with an immobilization device, positioning an insertion tool (e.g., a needle, a needle and marker wire, a needle gun, etc.) to be inserted into the target tissue on the immobilization device based on at least one reading of the target tissue, and inserting the insertion tool into the target tissue. An immobilization device for performing methods includes a frame assembly, a tissue immobilization assembly coupled to the frame assembly, the tissue immobilization assembly including a structure adapted to immobilize tissue, and a needle assembly releasably connectable to the frame assembly. The needle assembly includes a needle capable of being inserted into the immobilized tissue.

14 Claims, 21 Drawing Sheets

U.S. PATENT DOCUMENTS

| | | | | |
|---|---|---|---|---|
| 5,452,720 | A | * | 9/1995 | Smith et al. .................. 600/427 |
| 5,528,652 | A | * | 6/1996 | Smith et al. .................... 378/65 |
| 5,577,502 | A | | 11/1996 | Darrow et al. |
| 5,647,373 | A | | 7/1997 | Paltieli |
| 5,706,812 | A | | 1/1998 | Strenk et al. |
| 5,752,937 | A | | 5/1998 | Otten et al. |
| 5,776,062 | A | | 7/1998 | Nields |
| 5,787,886 | A | | 8/1998 | Kelly et al. |
| 5,868,673 | A | | 2/1999 | Vesely |
| 5,943,719 | A | * | 8/1999 | Feldman et al. ............. 606/130 |
| 6,102,866 | A | * | 8/2000 | Nields et al. ................ 600/461 |
| 6,119,033 | A | | 9/2000 | Spigelman et al. |
| 6,132,437 | A | * | 10/2000 | Omurtag et al. ............. 606/130 |
| 6,185,445 | B1 | * | 2/2001 | Knuttel ....................... 600/411 |
| 6,304,770 | B1 | * | 10/2001 | Lee et al. .................... 600/427 |
| 6,361,504 | B1 | * | 3/2002 | Shin ........................... 600/562 |
| 6,459,925 | B1 | | 10/2002 | Nields et al. |
| 6,731,966 | B1 | * | 5/2004 | Spigelman et al. .......... 600/407 |
| 2001/0053880 | A1 | * | 12/2001 | Selland ....................... 600/429 |
| 2003/0073934 | A1 | | 4/2003 | Putz |

FOREIGN PATENT DOCUMENTS

| | | |
|---|---|---|
| DE | 39 02 249 A1 | 8/1990 |
| DE | 42 25 112 C1 | 12/1993 |
| DE | 44 18 868 A1 | 5/1995 |
| DE | 199 02 521 A1 | 7/2000 |
| EP | 0 600 610 B1 | 6/1998 |
| FR | 2 719 760 | 11/1995 |
| WO | WO 93/14712 | 8/1993 |
| WO | WO 94/23647 | 10/1994 |
| WO | WO 96/11624 | 4/1996 |
| WO | WO 97/03609 | 2/1997 |
| WO | WO 97/29682 | 8/1997 |
| WO | WO 98/02097 | 1/1998 |

* cited by examiner

METHODS AND APPARATUS FOR PERFORMING PROCEDURES ON TARGET LOCATIONS IN THE BODY

BACKGROUND OF INVENTION

1. Field of Invention

The inventions described in this disclosure relate generally to apparatus and methods for performing medical procedures and, more particularly, to apparatus techniques for immobilizing tissue or providing frame of reference for performance of medical procedures.

2. Discussion of Related Art

The inventions described in this application relate generally to medical imaging and sensing of anatomical features, procedures performed in connection with that imaging and sensing, and the tools used for the procedures and sensing. The inventions will be described in the context of medical imaging for surgical procedures to be performed on soft tissue which is susceptible to movement during a procedure, such as a woman's breast, and more particularly related to marker placement (such as needle localization of implanting or injecting a marker), biopsies and open surgical removal of a suspected cancerous lesion within a breast. While certain aspects of the present inventions are uniquely well-suited to one or more of these applications, this is not intended to be limiting with respect to all aspects of the inventions described herein.

Mammography is presently the primary method for screening for breast cancer. The primary role of mammography is to screen asymptomatic women in order to detect breast cancer at an earlier stage than would occur with only self-examination and/or clinical breast examination. Detection at an earlier stage of the disease has been shown to reduce or delay mortality from breast cancer.

Mammography uses X-rays to create an image of the interior of the breast. Mammography typically requires careful positioning of the patient by a highly skilled technician trained in mammographic technique. Optimum results depend on pulling and squeezing of the breast during the mammogram, which can be painful. Accurate results are also highly dependent on interpretation of films by a radiologist.

When a patient is screened by mammography, a "suspicious mass" or lesion that is non-palpable (cannot be felt by touch) and not visible to the naked eye is often identified. In these cases, it must be determined whether the lesion is cancerous. This often requires that the lesion or a piece of the lesion be removed for further investigation. To do this, of course, there must be some way that a surgeon can find the lesion in the breast (referred to as "tumor localization" and also as "lesion localization").

A biopsy is a procedure for removing a portion of the lesion for the purpose of determining whether the lesion is malignant. There are at least three methods of biopsy: open surgical biopsy, core needle biopsy and fine needle (aspiration) biopsy.

For open surgical biopsy, lesion location can be established through a procedure called pre-operative needle localization. Needle localization begins when a specially trained technician puts the breast into a specialized mammography fixture. Several views of the breast are taken using standard mammography to determine the approximate location of the "suspicious mass."

To locate a lesion, frequently, the breast is squeezed between plates horizontally and one image is taken. The plates are removed and repositioned so that the breast is squeezed vertically and another image is taken and the plates removed again. In addition, multiple images may be taken until the lesion is located. A trained specialist then uses the two (or more) two-dimensional images to estimate where the lesion may be located in three-dimensional space.

A needle is then placed into the breast at the estimated lesion location. The placement of the needle is verified through mammography, again using two or more two-dimensional images. Needle insertion and verification may be repeated until the placement is deemed appropriate by a radiologist. A small wire with a J hook is then placed through the core of the needle. Alternatively, the wire may be pre-loaded in the needle. The needle may be removed and the wire remains. Otherwise, the wire remains in the needle. At this point, the needle localization procedure is complete. The patient is then moved to a surgical setting. During surgery, the wire is used as a guide for the surgeon to cut to the "suspicious mass." When the surgeon reaches the area where the wire terminates, a tissue sample is taken. The sample is verified to be that of the identified "suspicious mass" by comparing a mammogram of the tissue sample with that of the original mammography.

In practice, depending on breast size, however, there is often as much as a ½ inch movement of the wire before or during the procedure. Accordingly, the sample tissue may not have come from the "suspicious mass." In those cases, the surgeon may search around the wire termination point and repeat the sample and verification procedure until a match is found. The wire can drift away from its original position in response to motion of the breast. The extent of wire drift may increase as the length of time between localization and surgery increases and as the breast moves. Mammography is used repeatedly in many aspects of breast cancer screening and diagnosis. For example, a dozen mammographic X-rays may be required in support of a single open surgical biopsy.

In core biopsy procedures, a tool is positioned within the breast. The breast is then imaged to determine location of the tool with respect to the lesion. The tool may then be repositioned to more closely target the lesion. This process can be cumbersome and require multiple images of the breast.

In many cases, where the lesion is determined to be cancerous, the lesion must be surgically removed. When the breast is to be largely preserved and only the lesion removed, the procedure is called a lumpectomy. A lumpectomy sometimes requires needle localization as described above. Instead of taking a piece of the "suspicious mass" for analysis, however, the entire mass is surgically removed.

Because the wire may move during or before the procedure due to compression and/or re-compression of the tissue, the biopsy and excision procedures often target the suspicious mass inaccurately. As a result, the procedures may be lengthier than would otherwise be required, occasionally unsuccessful due to failure to accurately localize the lesion, and may result in the unnecessary removal of healthy tissue from the breast. Some (but not all) embodiments of the present invention address one or more of these issues as well as having other advantages that would be apparent to one of ordinary skill in the art based on the disclosure provided herein.

SUMMARY OF INVENTION

One aspect of the invention is directed to a method of performing a medical procedure on target tissue within the body, the method comprising: immobilizing the target tissue with an immobilization device; positioning an insertion tool (e.g., a needle, a needle and marker wire, a needle gun, etc.) to be inserted into the target tissue on the immobilization device based on at least one reading of the target tissue; and inserting the insertion tool into the target tissue.

In embodiments of the invention, the method further comprises taking at least one reading of a location of target tissue, and particularly, comprises taking a first mammography reading. The step of taking at least one reading of a location of target tissue comprises taking a second mammography reading. The method further comprises plotting the first and second mammography readings on an image grid, wherein a first distance from a known reference point on the immobilization device is determined from indicia on the image grid to position the needle, and correcting for at least one anomaly created by the first and second mammography readings. The plotting of the first and second mammography readings on the image grid may be generated by a PDA. The method further comprises performing a medical procedure on the target tissue, wherein the step of performing a medical procedure is selected from a group comprising one of the following: needle localization; needle aspiration; vacuum-assisted biopsy; virtual guided breast surgery; open surgical biopsy; in-office biopsy; sentinel node biopsy; and imaging correlation and implantation. The immobilization device may be attached to a unit to perform the medical procedure. The method further comprises placing a marker wire within the needle to mark the target tissue. The method further comprises adjusting the immobilization device to compress tissue surrounding the target tissue. The method further comprises performing at least one diagnostic procedure to obtain the at least one reading of the target tissue. The immobilization device may be attached to a mammography unit to take the at least one reading. The method further comprises determining a length of a needle to be inserted into the target tissue.

In another aspect of the invention, an immobilization device comprises a frame assembly, a tissue immobilization assembly coupled to the frame assembly, the tissue immobilization assembly including a structure adapted to immobilize tissue, and a needle assembly releasably connectable to the frame assembly. The needle assembly includes a needle adapted to be inserted into the immobilized tissue.

In embodiments of the invention, the frame assembly includes a frame member constructed and arranged to mount the immobilization assembly thereon. Specifically, the frame assembly further includes a seat configured to receive and secure the tissue immobilization assembly, the seat being adjustably secured to the frame member to adjust the position of the immobilization assembly with respect to the frame assembly. The frame assembly further includes at least one rod secured to the seat and adjustably secured to the frame member. The structure of the immobilization assembly comprises a bottom wall and two side walls formed with the bottom wall, the bottom and side walls being sized to receive the tissue to be immobilized, and a top wall slidably connected to the side walls. The immobilization device further comprises means for securing the top wall in place with respect to the side wall. Particularly, the means for securing the top wall in place with respect to the side wall comprises a serrated area formed on the top wall adapted to mate with a serrated are formed on at least one of the side walls. Each side wall has at least one slot formed therein. The slot is adapted to receive a positioning detent, which is formed along an edge of the top wall. The top wall is secured in place by at least one inverted U-shaped member, the at least one inverted U-shaped member being positioned adjacent a side wall and formed with the top wall. An outwardly facing surface of the at least one inverted U-shaped member has the serrated area adapted to mate with the serrated area formed on the respective inner facing surface of its respective side wall to secure the top wall in place with respect to the side wall. The needle assembly comprises a needle holder capable of being secured to the frame assembly. The needle holder includes an outer sleeve having a clamping assembly formed therewith adapted to be releasably clamped to the frame assembly. The needle holder further includes a tubular member and a needle portion adapted to be axially received within the outer sleeve.

In yet another aspect of the invention, a method for performing a medical procedure on target tissue comprises: immobilizing the target tissue; performing a diagnostic procedure on the immobilized target tissue; and performing a medical procedure on the immobilized target tissue.

In embodiments of the invention, the step of performing a medical procedure is selected from a group comprising one of the following: needle localization; needle aspiration; vacuum-assisted biopsy; virtual guided breast surgery; open surgical biopsy; in-office biopsy; sentinel node biopsy; and therapeutic imaging correlation and implantation. The step of immobilizing the target tissue comprises affixing an immobilization device to tissue surrounding the target tissue, and adjusting the immobilization device to compress the tissue surrounding the target tissue. The step of performing a diagnostic procedure comprises performing a scan of the target tissue. The step of performing a scan of the target tissue comprises taking at least one image of the target tissue. The method further comprises determining a position of the target tissue based the at least one image of the target tissue. The method further comprises calculating a location of the target tissue with respect to a known reference point. The method further comprises plotting the location on an image grid. The step of performing a medical procedure comprises inserting a needle into the target tissue, wherein inserting a needle into the target tissue comprises determining a needle entry direction, a needle entry location, and a depth of needle penetration. The method further comprises placing a marker wire within the target tissue.

In another aspect, a frame assembly, capable of supporting an immobilization assembly and further adapted to be attached to a device, comprises a frame member adapted to be attached to the device, and a seat, coupled to the frame assembly. The seat is adjustably secured to the frame member to adjust the position of the immobilization assembly with respect to the frame assembly. The frame assembly further includes at least one rod secured to the seat and adjustably secured to the frame member.

Another aspect of the invention is directed to an immobilization assembly for immobilizing tissue upon which a medical procedure is to be applied. The immobilization assembly comprises a bottom wall and two side walls formed with the bottom wall, the bottom and side walls being sized to receive the tissue to be immobilized, and a top wall slidably connected to the side walls.

In embodiments of the invention, each side wall has at least one slot formed therein, each slot being adapted to receive a positioning detent, which is integrally formed along an edge of the top wall. The top wall is secured in place by two inverted U-shaped members, each member being positioned adjacent a respective side wall and integrally formed with the top wall. An outwardly facing surface of each inverted U-shaped member has a serrated area adapted to mate with a serrated area formed on the respective inner facing surface of its respective side wall to secure the top wall in place with respect to the side walls. In another embodiment, the serrated area is formed on the top wall adapted to mate with a serrated are formed on at least one of the side walls to secure the top wall in place with respect to the side walls.

A further aspect of the invention is directed to a needle assembly adapted to be attached to an immobilization device, the needle assembly comprising a needle holder including an outer sleeve having a clamping assembly formed therewith adapted to be releasably clamped to a frame assembly of the immobilization device, and a tubular member and a needle portion adapted to be axially received within the outer sleeve.

In embodiments of the invention, the outer sleeve of the needle holder includes a crease, the crease enabling the needle holder to be flexed apart to remove the needle holder from the tubular member and the needle portion without removing the needle portion from the tissue.

Another aspect of the invention is directed to a kit for use in a medical procedure on tissue. The kit comprises an immobilization assembly, and a needle assembly comprising a needle holder including an outer sleeve having a clamping assembly formed therewith adapted to be releasably clamped to a frame assembly of the immobilization device, and a tubular member and a needle portion adapted to be axially received within the outer sleeve.

A further aspect of the invention is directed to a method of performing a procedure on an area of interest in a breast. The method comprises steps of: placing an immobilization device on the breast; taking a first image of the tissue in the immobilization device from a first direction; taking a second image of the tissue in the immobilization device from a second direction at an angle different from the first direction; and removing the immobilization device.

In embodiments of the invention, the method further comprises a step of performing a medical procedure on the breast, before the step of removing the immobilization device. The method further comprises a step of compressing the tissue of the breast in the immobilization device. The method further comprises a step of attaching the immobilization device to an imaging unit.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION OF THE PREFERRED EMBODIMENTS

Figure 1:
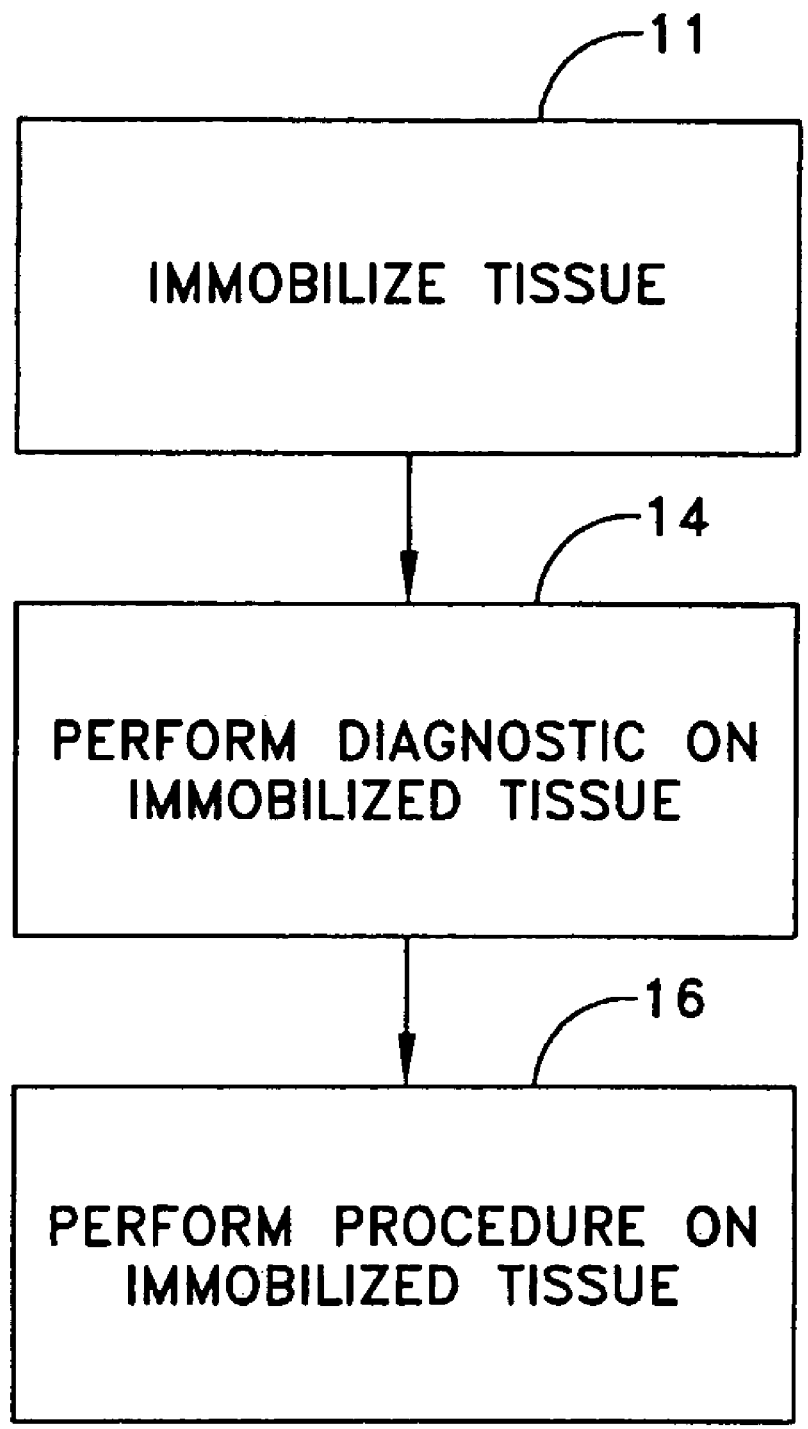
FIG. 1 is one embodiment of a method of performing a diagnostic procedure on soft tissue.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," or "involving", and variations thereof herein, is meant to encompass the items listed thereafter and equivalents thereof as well as additional items.

In one aspect of the inventions, improvements are made to procedures for examining lesions within a breast. Application of the inventions, however, is not limited to this context in every aspect of the inventions. Various features of the inventions may be applied to sensing or imaging or immobilizing any soft organ or tissue, imaging hard features, and imaging external as well as internal features. Certain embodiments of the invention are particularly well suited for imaging a portion of the body that is composed primarily of soft tissue, where the soft tissue can move or change shape during the procedure (such as a lesion within a breast moving in response to movement of the skin of the breast or when the shape of the breast is changed through manipulation). While the detailed description presents the invention in the context of procedures for examination or removal of a lesion within a breast, this is not intended as limiting for all embodiments.

While the inventions are also described with reference to examples using X-ray localization of tumors, this is not intended as limiting. MRI technology, PET, computer tomography, ultrasound, "real-time" ultrasound and other diagnostic internal imaging techniques may be used in the context of breast cancer diagnosis and treatment as well as in other applications.

FIG. 1 is an illustration of one embodiment of using certain aspects of the present invention. At step 11, the tissue being examined (for example, a breast) is immobilized. In certain embodiments, this may be done using the apparatus and procedures described below.

At step 14, the diagnostic procedure is performed with reference to the immobilized tissue. For example, a breast may be immobilized at step 11 and then scanning procedures may be performed to detect a lesion within the breast. In one embodiment, the taking of two X-rays, at different, multiple (e.g., orthogonal) angles is performed.

In many instances, in the prior art, the taking of these X-rays at different angles is done with reference to soft tissue that has been manipulated between the images. For example, plates may be oriented horizontally and used to flatten the breast for one image and then re-oriented vertically to squeeze the breast in the opposite direction for a second image. The order of the images (e.g., horizontal then vertical) may be changed for some embodiments and is not intended as limiting; simultaneous imaging is also possible in some embodiments. Indeed, one or more images may be taken on a diagonal and the images may (but do not have to) be from orthogonal angles.

According to certain aspects of the present invention, the diagnostic is performed with reference to immobilized tissue. Thus, where more than one image is taken of the immobilized tissue, that tissue is kept as free from movement as is practical for each of the two images. In certain embodiments, this reduces or eliminates the amount of movement of the lesion within the breast between images, permitting in some cases a more accurate estimation of where a lesion is by maintaining the lesion as close as practical to the same position for each of the two images. In other embodiments, an immobilization device is used to control movement between images, such as when a breast is compressed more along one axis for a first image and compressed on a different axis for a second image. By more precisely controlling movement between images, any movement of the lesion may be controlled and/or better accounted for.

At step 16, the medical procedure is performed. As described above, while this example includes biopsies performed with respect to a lesion within a breast, many of the present inventions are suitable for other medical procedures performed with respect to the breast or other tissue. For example, the procedure may be any of the procedures described herein, with reference to a medical procedure performed on a breast.

According to certain embodiments of the present invention, the tissue remains immobilized between the scanning or diagnostic tests performed at step 14 and the performance of the medical procedure at step 16. In these embodiments, the amount of possible movement of the lesion between the time of scanning and the time of performance the medical procedure can be reduced or eliminated.

In other embodiments, however, the scanning steps are used to place a localization device within the breast. In these embodiments, the immobilization device may be removed for performance of a subsequent diagnostic test (e.g., biopsy) or other surgical procedure. For example, the immobilization device may be used to place a wire within the breast, where the tip of the wire is located within the suspicious mass. Other localization devices may include marker deposition for example by injecting a die. Such localization procedure may be used to identify a point within the breast where a subsequent procedure will be performed, such as tissue removal, core biopsy, and/or vacuum-assisted biopsy.

Figure 2:
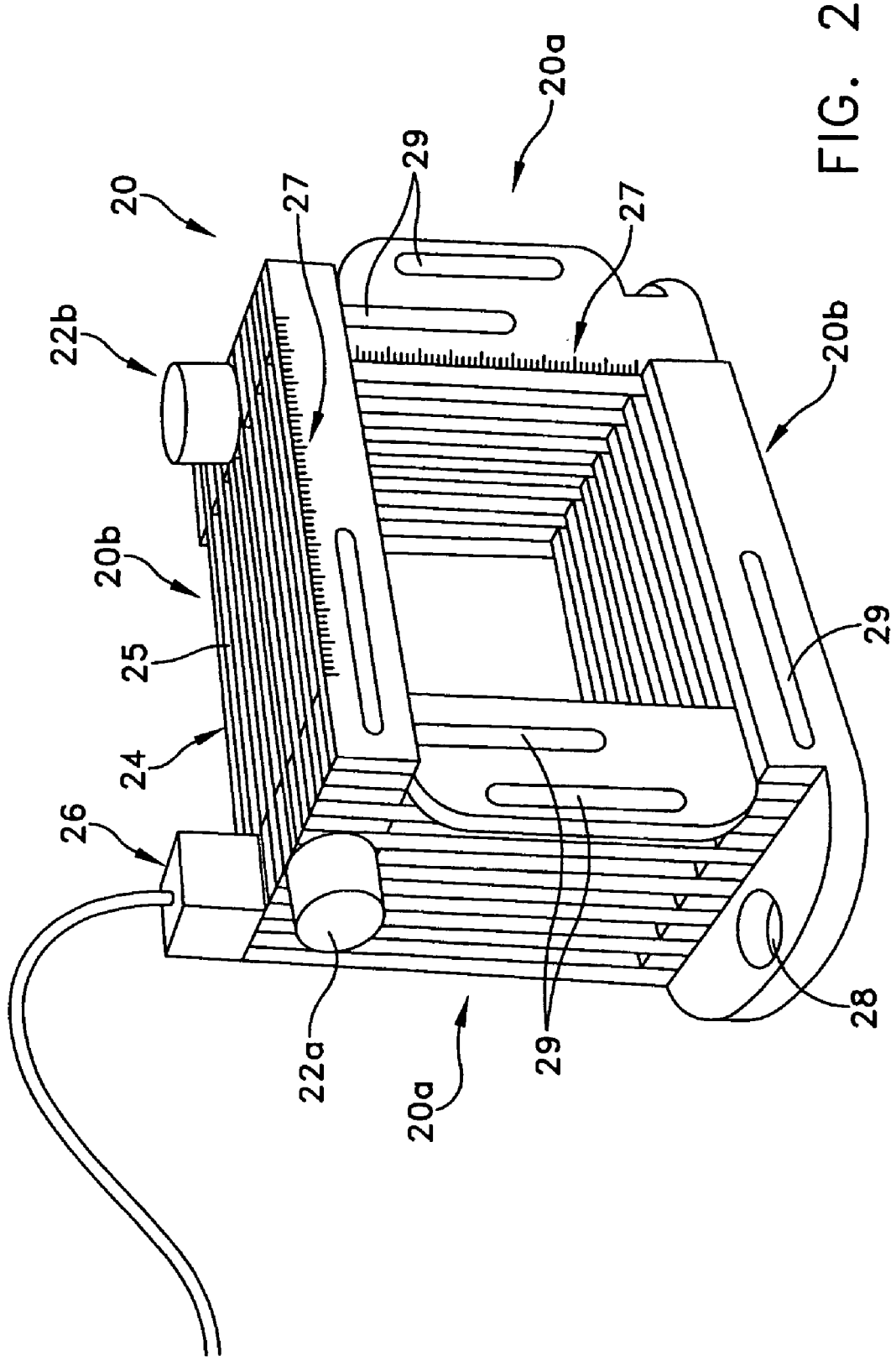
FIG. 2 is one embodiment of a tissue immobilization device and, more specifically, a breast immobilization device.

FIG. 2 illustrates one embodiment of an immobilization device 20. This particular immobilization device is suitable, for example, for use in taking a biopsy of a lesion within a breast. In this particular example, the immobilization device 20 is of a square shape. Thus, the immobilization device is symmetric with respect to two axes. This may, for example, correspond to the direction of taking of two separate x-rays, one x-ray being taken orthogonal to side 20a and the other being taken orthogonal to the side 20b.

While the embodiment of FIG. 2 bears certain advantages for some embodiments of the present invention, other shapes could be employed in an immobilization device. For example, an immobilization device could be configured in a circular or elliptical fashion. Similarly, the immobilization device may have planar sides, such as the four-sided device of FIG. 2, or may have more or fewer planar sides. Similarly, for embodiments with planar sides, the edges where two planar sides meet may be rounded, to reduce the risk of pinching during operation of the device as described below.

Knobs 22a and 22b may be used to adjust the size of the device 20. For example, the knobs 22a and 22b may be turned in order to compress the breast. Thus, knob 22a could be turned clockwise to cause the sides 20a to move closer together. Knob 22a could be turned counterclockwise to cause the sides to move further apart. The knobs may include a device (not shown) permitting the knob to be locked in place. Such a mechanism may prevent inadvertent loosening of the device after scanning or during the medical procedure. Such a mechanism may include a push button, latch or other device. The knob may also include a quick release mechanism (not shown) that would allow the plates to quickly come apart. This may be used for removal of the device quickly if the patient experiences extreme discomfort, and also to ease removal of device in the normal course of operation.

In the embodiment shown in FIG. 2, knob 22a causes sides 20a to move in and knob 22b causes sides 20b to move closer together or further apart. In another embodiment, a single knob could be used causing both sides to move in and out together. This may be advantageous in circumstances where it is desirable to have a common distance between each of the sides 20a and sides 20b.

While the embodiment illustrated in FIG. 2 uses a simple mechanical device for positioning sides, such as a bolt and screw, an electromechanical device or other mechanism for causing the sides to move relative to each other could be used, as would be apparent to one of ordinary skill in the art based on the disclosure provided herein. For example, current technology includes a variety of mechanisms for precise automatic computer-controlled movement, with open and closed loop control, for pick and place machines used in various manufacturing applications.

The embodiment of FIG. 2 uses a chamber frame as shown, constructed of a rigid, nonmagnetic and radio-translucent material. In this example, the chamber frame is rigid in order to minimize the movement of the soft tissue (e.g., breast) during the procedure in between scanning and procedures. Softer materials may be used in any context in which the loss of accuracy (if any) caused by permitting additional movement of the breast between scanning and procedure is acceptable. Thus, in some context, an immobilization device may be constructed using a semi-rigid material (such as certain rubbers, which have some flexibility to deform in use but also some rigidity to resist deformation once the device is affixed to a patient), a flexible material, or a combination of rigid, semi-rigid and flexible (e.g., portion of the chamber being rigid such as a hard plastic and portions being flexible, such as cloth) so long as the soft tissue is sufficiently immobilized for the particular procedure being performed. In addition, certain soft materials can be used to provide an exterior shell with materials enclosed that have volume-filling properties such as various gels. Additionally, certain materials that exhibit "memories" of shape and volume may be used or materials which are malleable but can be hardened, for example by change in temperature or by application of an electric field, a chemical or exposure to air (e.g., by drying to a hardened state). For the latter, the immobilization device may be fitted to the patient in its more malleable form and then "hardened" (made less malleable) to a less malleable form.

The chamber frame may be constructed of a material that does not hinder one or more scanning modalities, for example, where the chamber is configured in a way that portions of the chamber cover a portion of the target area, the chamber being made of a material that is translucent with respect to the imaging apparatus being used. In the device 20 of FIG. 2, radio-opaque markings 27 are also included on the chamber frame. These radio-opaque markings may appear on the x-ray image and be visible to the medical professional as well. Where this is done, a more precise orientation of a medical instrument with respect to the chamber may be made, with reference to radio-opaque markings on an x-ray or other image.

The immobilization device 20 includes both rigid portions (or semi-rigid portions) 24 and openings 25 between them. In this example, the openings 25 are provided to provide access for surgical instruments. For example, a biopsy needle may be inserted through an appropriate opening. The configuration of the openings in FIG. 2 is illustrative only and may be optimized for the particular procedure or procedures that the immobilization device 20 is intended to support.

The immobilization device 20 may include a mechanism to permit it to be attached to various medical equipment. For example, slots 29 could be provided in an appropriate configuration to permit the immobilization device to be attached to an x-ray imaging system. This would permit the device 20, and therefore the breast, to be more accurately and reproducibly positioned with respect to the x-ray equipment. Additional mechanisms could be connected to the device 20, for example, by using openings 28, to permit the immobilizations device 20 to interface to different types of equipment, such as other types of imaging equipment, as well as surgical equipment.

By allowing the immobilization device 20 to be removably connectable to different medical equipment, the immobilization device can be connected to an apparatus for screening and connected to a separate apparatus for performing a procedure, such as a biopsy. An interface that allows mechanical or automated control to coordinate any procedures may be further provided.

The immobilization device 20 may include an interface unit 26 for control of the device. For example, the device may be equipped to sense pressure on the walls of the device, as a safety measure to ascertain how hard a device is squeezing the breast. This may be done by incorporating sensors into the immobilization device 20. In the alternative, a liner may be used with the immobilization device 20 which can assist with sterilization and comfort. If so, in some embodiments, pressure sensing devices could then be incorporated in the liner.

The interface may further include a mechanism to automate the control of the tightening and loosening of the sides of the immobilization device 20. Thus, for example, the knobs 22a and 22b could be driven through the interface 26. Where this is done, pressure sensing devices may further be used as a safety measure to assure that too much pressure is not being applied to the breast.

The immobilization device 20 may also have heating and/or cooling elements built into the device, or incorporated into a liner for use with the device. Where this is done, the heating and cooling of the tissue within the immobilization device 20 may also be controlled through interface 26.

In some embodiments, temperature sensors may also be incorporated, to monitor the temperature of the tissue. A feedback loop may be formed to control heating and/or cooling of the tissue to maintain an appropriate temperature for either comfort or the particular medical procedure being performed.

The immobilization device 20 may further include indicia for the setting for the compression of the device, e.g., how close together the sides are. Thus, where the immobilization device is applied repeatedly over time, a medical practitioner could assure that the device settings are the same each time, increasing the chance that the immobilization device is placed on the patient in the same configuration. Such indicia may include, for example, markings on the knobs 22a and 22b, marking on the sides or edges of the device, or some other mechanism that would be readily apparent to one of ordinary skill in the art based on the disclosure provided herein.

Whether used in conjunction with sensors (such as pressure or temperature sensors) or not, a liner may be provided for use with the immobilization device 20. Such a liner may be shaped for use in connection with immobilization device 20 and may be sterilized where a surgical procedure is being performed. Such liners may be provided, and pre-sterilized, in packaged separate units.

The openings 28 may also be used to attach the immobilization device 20 to a mobile transfer unit. For example, if a patient is to be transported between rooms in a wheelchair, the wheelchair could be fitted with an interface that also permits the immobilization device to be attached to the wheelchair.

In certain embodiments of this aspect of the inventions, a unit is adapted to attach in a fixed manner to the wheelchair to provide an interface on the wheelchair for an immobilization device.

In certain embodiments, a wheelchair may be adapted specifically to permit the patient to remain seated in the wheelchair during the scanning and/or surgical procedure. This promotes the reduction of relative movement between the patient and the immobilization device, thereby reducing any movement of the breast with respect to the immobilization device and/or the lesion within the breast. Thus, for example, a wheelchair could be designed or specially adapted to firmly fix the position of the patient and the immobilization device in a manner restricting movement of the patient relative to the immobilization device and the wheelchair.

In other embodiments (or this one), the immobilization device may be made of a lightweight material, to make the device easier to hold in place when supported by the patient and to reduce discomfort. As one example, a variety of plastics such as a polycarbonate, a polyethylene or a polypropylene, may be used.

Figure 3:
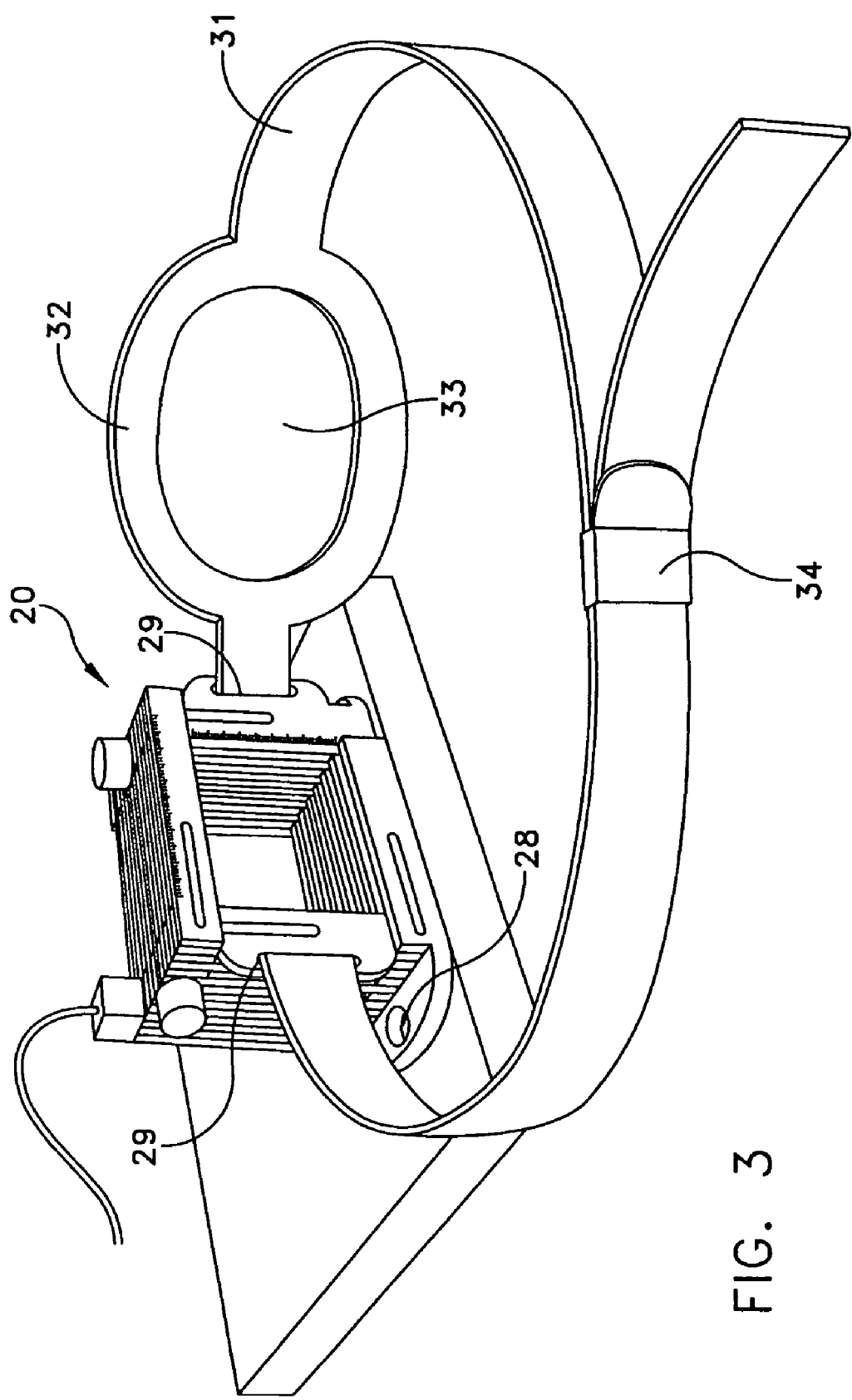
FIG. 3 is one embodiment of a breast immobilization device including a harness.

FIG. 3 illustrates one embodiment of another mechanism for attaching an immobilization device 20 to a patient. In this embodiment, a chest strap 31 is provided. The chest strap may be positioned around the patient when the immobilization device has been attached. The belt may be fastened or tightened as indicated at 34 using for example a suitable mechanism. An opening 33 is provided to accommodate the second breast of the patient and to help maintain the immobilization device in a constant relationship to the patient, to reduce movement of the breast in the immobilization device and to reduce possible movement of the lesion within the breast.

In this example, the belt 31 is attached to the immobilization device through the slots 29. Openings 28 are used to attach the immobilization device 21 either to a mobile transport unit such as a wheelchair or instead to scanning equipment or equipment that performs the surgical procedure.

Figure 4:
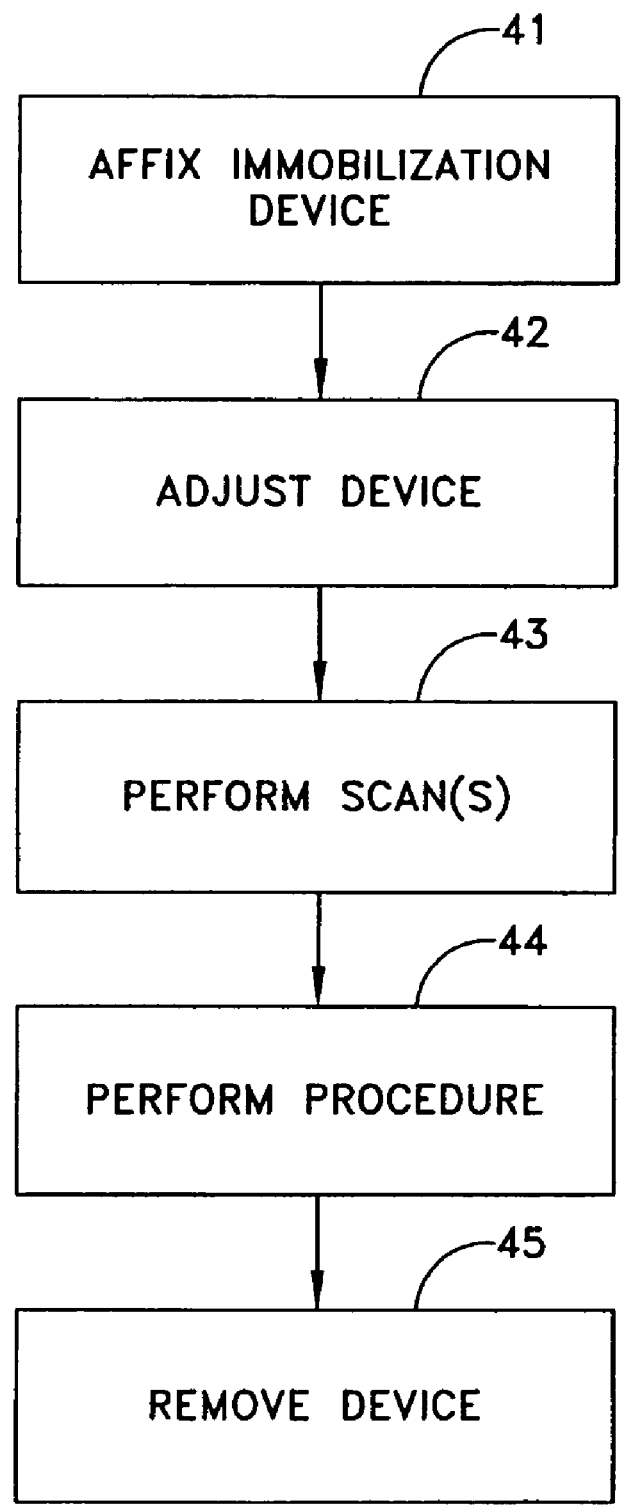
FIG. 4 is one embodiment of a method for performing a medical procedure using an immobilization device.

FIG. 4 illustrates one embodiment of a method for using an immobilization device, such as the one described above. In step 41, the device is affixed to the patient. As described above, this may, in some embodiments, involve the use of a belt or mobile device permitting the patient to be moved from location to location (or both).

In step 42, the device is adjusted for a snug fit with respect to the patient. As described above, this may be done manually or automatically. In some embodiments, as a safety measure or to help assure the patient's comfort or to help assure a proper fit, pressure sensors may be used to assure that a sufficient (but not too large) amount of pressure is being applied to compress the breast. An automatic release (or loosening) mechanism may be provided where a pressure threshold is exceeded.

At step 43, a scanning and/or imaging procedure (or procedures) is performed. As described above, this may permit isolation of a lesion within a breast (as one example). In certain embodiments, the immobilization device 20 will include markings that permit a technician or computer to analyze the position of the lesion with reference to the immobilization device.

In some embodiments, it may be necessary or desirable to take an asymmetric scan. For example, if the breast of the patient being examined is compressed symmetrically, in some circumstances, it may be possible that a clearer image cannot be taken through the breast, without first reducing the thickness of the tissue through which the x-rays pass. In this circumstance, the immobilization device 20 may be adjusted out of an asymmetric position to permit more than one shape during scanning. Thus, the device may be used to flatten the breast horizontally for one scan, and then adjusted to flatten the breast vertically for a second scan.

While use of an immobilization device in this fashion may increase the possibility that the lesion moves during scanning, and may in some circumstances reduce accuracy, the use of the immobilization device is still preferable in some embodiments because it reduces and better controls the amount of movement between scans. By keeping the immobilization device affixed to the patient during both, and adjusting it between scans, the relative movement of a breast between scans and before the procedure may be reduced and controlled. For the latter, a better feel for lesions movement (or automated monitoring of lesion movement, or automated estimation of lesion movement) may be maintained.

At step 44, the medical procedures performed are based on the scan. In some embodiments, the immobilization device is maintained on the patient during scanning at step 43 as well as the medical procedure at step 44. Where the two are separated substantially in time or location, however, there may be circumstances where the immobilization device may be removed. If so, use of the immobilization device may still assist reproducibility, provided that the patient may be refitted with the immobilization device for the medical procedure and the practitioner (preferably) endeavors to attach the device in the same position as it was affixed during the scanning procedure. Some examples of techniques for performing this are provided below, but are not intended to be limiting for all aspects of this embodiment of the invention.

At step 45, after the medical procedure has been performed, the immobilization device may be removed.

Figure 5:
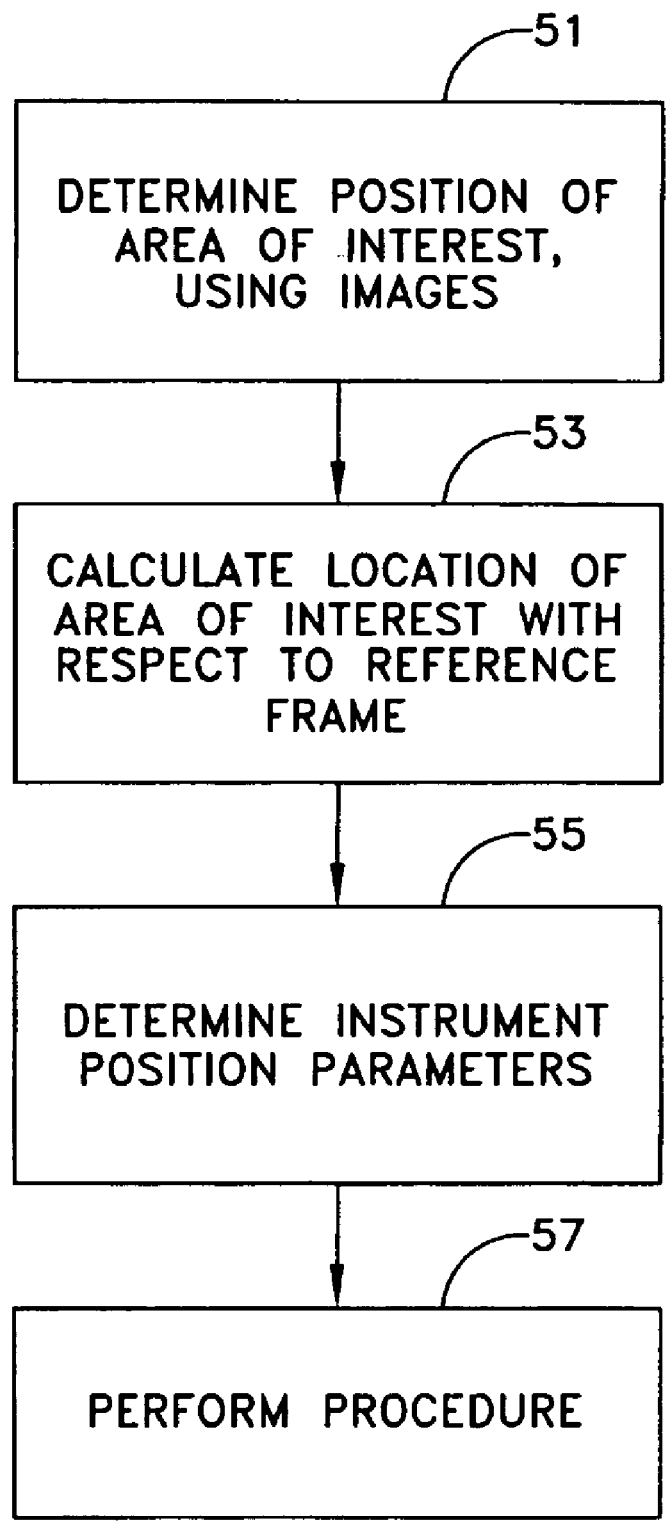
FIG. 5 is one embodiment of a method of performing a medical procedure with respect to a reference frame, such as that provided by an immobilization device.

FIG. 5 illustrates one embodiment of a method for performing a procedure. Any of a number of procedures could be performed using this particular embodiment of the present invention. For example, the procedure could be needle localization, needle aspiration, vacuum-assisted biopsy, virtual guided breast surgery, in-office biopsy, sentinel node biopsy or therapeutic imaging correlation and implantation.

At step 51, the position of an area of interest is determined using images. For example, if the images are two x-rays taken to isolate a lesion within a breast, the three-dimensional locations of the lesion may be determined or estimated. This calculation may be made with reference to a flame of reference that corresponds to one or more locations or markers on the immobilization device. As described above, this can be done with reference to radio-opaque markings on the immobilization device, at least in certain embodiments.

At step 53, the location of the area of interest is determined with respect to a reference frame. That reference frame may correspond to the immobilization device or something whose position is known relative to the immobilization device. Thus, the location and three-dimensional space of the lesion with respect to a reference point, such as one or more points on the immobilization device, can be determined.

Using location and imaging techniques known in the prior art and as described in, for example, U.S. Pat. No. 6,119,033, issued Sep. 12, 2000 and naming Spigelman et al. as inventors, which is fully incorporated herein by reference, an image may be displayed during a medical procedure being performed on the area of interest.

Returning to the embodiment disclosed in FIG. 5, at a step 55, the positioning parameters for an instrument may be determined. This calculation may be performed by hand, or may be implemented on a computer system using hardware and/or software. In this example, at step 55, the positioning parameters may include a point of entry and orientation for the surgical instrument as well as a depth. Thus, for example, a medical practitioner or computer may calculate a position on the breast (e.g., with reference to the immobilization device) where a surgical instrument should enter, and an angle (with respect to the immobilization device) at which the instrument or needle should be inserted. In addition, a depth of insertion could also be calculated. If depth markings are included on the surgical instrument, a calculation can be made which permits relatively automated positioning and insertion of the surgical instrument. In certain embodiments, positioning units or tools such as guide ramps or tubes may be provided and directly or indirectly attached to (or incorporated into) the immobilization device at an appropriate place to help position and guide the tool. For certain of these embodiments, the immobilization device may include one or more interfaces for allowing positioning units or tools to be (in some embodiments, adjustably) to be attached to the immobilization device at one or more appropriate positions.

While this can be used to assist the hand insertion of the surgical instrument, in other embodiments, the surgical instrument may be inserted using an automated tool or mechanical arm.

At a step 57, the procedure is performed using the calculated instrument position parameters.

As one of ordinary skill in the art would readily appreciate, based on the disclosure provided herein, a number of different mechanisms may be used both for specifying lesion location with respect to a reference frame and for calculating the parameters for positioning and insertion of the surgical instrument. For example, xyz coordinates may be used to specify location of the center of a lesion with respect to the immobilization device. In other embodiments, polar coordinates could be used. Any particular reference frame may be used.

As described above, the surgical instrument may include markings so that the depth of insertion can be ascertained for verification with reference to the desired insertion depth. In other embodiments, the surgical instrument could be marked at the desired insertion depth prior to performing the surgical procedure. The instrument may then be inserted to the marked depth.

Figure 6:
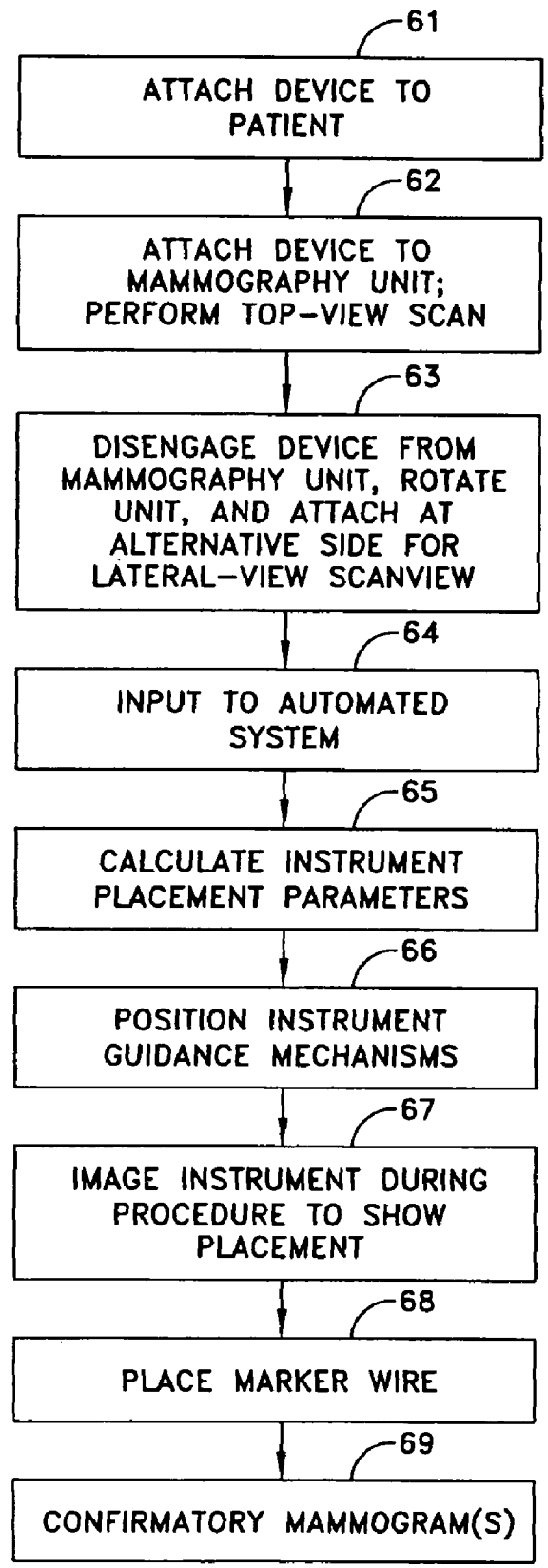
FIG. 6 is one embodiment of a method using an automated system to assist in locating an area of interest (such as a lesion) in a patient.

FIG. 6 illustrates one embodiment of a method for performing needle localization. This embodiment illustrates certain independent aspects of the present inventions.

At a step 61, an immobilization device, such as those described according to one of the embodiments herein, is attached to the patient.

At a step 62, the immobilization device is attached to a mammography unit. This may be done, for example, using the openings 28. A top view, for example, scan is performed with the device attached to the mammography unit. Side views and orthogonal views may also be taken as well. Preferably, the attachment mechanism is adapted to provide a secure fit with existing units. Optionally, adapters may be provided for use with an immobilization device to permit it to be used with more than one type of mammography unit, or to other types of medical equipment such as other imaging devices.

At step 63, the device is disengaged from the mammography unit, to permit it to be rotated. The device is reattached at an alternative side of the immobilization device to permit a lateral image to be taken. At this step, the immobilization device may be attached, for example, using slots 29.

At a step 64, the images may be input to an automated system that assists in performance of the surgical procedure (at least according to certain embodiments).

At step 65, instrument placement parameters may be determined. As described above, this can be done with reference to the immobilization device using calibration indicia located on the device. Also as described above, this may be done either by a medical practitioner or in an automated fashion.

At a step 66, according to certain embodiments of the present inventions, instrument position guidance mechanisms are affixed to the immobilization device. In other embodiments, the mechanism may be already engaged to the immobilization device. Here, a mechanism to fix the motion of the instrument relative to the immobilization device, and therefore the lesion, may be used.

At a step 67, according to certain embodiments, an image of the instrument relative to the immobilization device and/or the lesion can be displayed on a monitor. The technology for doing so has been described in general in U.S. Pat. No. 6,119,033 cited above. According to certain embodiments of the present inventions, however, the portion of the body being viewed is immobilized rather than being permitted to change shape. In this sense, the technology for imaging can be simpler, because calculations for lesion movement relative to changes in the shape of soft tissue (e.g., a breast) may not need to be accounted for in certain embodiments. In other embodiments, however, calculations about lesion movement during multiple scanning procedures can be performed. For example, if the shape of the breast is altered within the immobilization device during two different scanning procedures, a calculation can be made in an effort to more precisely identify the location of the lesion. This calculation may be performed as described in the above referenced patent.

At step 68, a marker wire may be placed to show where the surgical instrument was positioned for the procedure. The position of the marker wire may be held constant within the soft tissue (e.g. a breast) using the immobilization device.

At a step 69, a confirmatory mammogram or mammograms may be taken to establish that the procedure was performed within the lesion. The method for performing one or more confirmatory mammograms may include maintaining the breast within the immobilization device during the performance of confirmatory scans.

In the method described in FIG. 6, previously taken screening mammograms (e.g., top and lateral view of the breast) may also serve as controls during performance of the procedure. Needle aspiration may be performed using a similar method to that illustrated in FIG. 6, according to certain embodiments of the present inventions. Similarly, vacuum-assisted biopsies may be performed, using a vacuum-assisted device rather than a needle aspiration device.

According to alternative embodiments of the present inventions, the medical procedure can be guided virtually, using a monitor to display an initial tool position and lesion location or orientation and with respect to the immobilization device and/or breast. In one embodiment, the patient can remain attached to the imaging machine, such as a mammography unit. This may permit images to be taken during the procedure, or for certain equipment, a continuous display. In other embodiments, the immobilization device may be attached to a fixed surface other than the imaging equipment. Doing so will reduce the risk that patient movement during the procedure can adversely affect the outcome.

As described above, for these procedures as well as others, heating and/or cooling may be applied to either assist in performance of the procedure or to make the patient more comfortable, or both.

Figure 7:
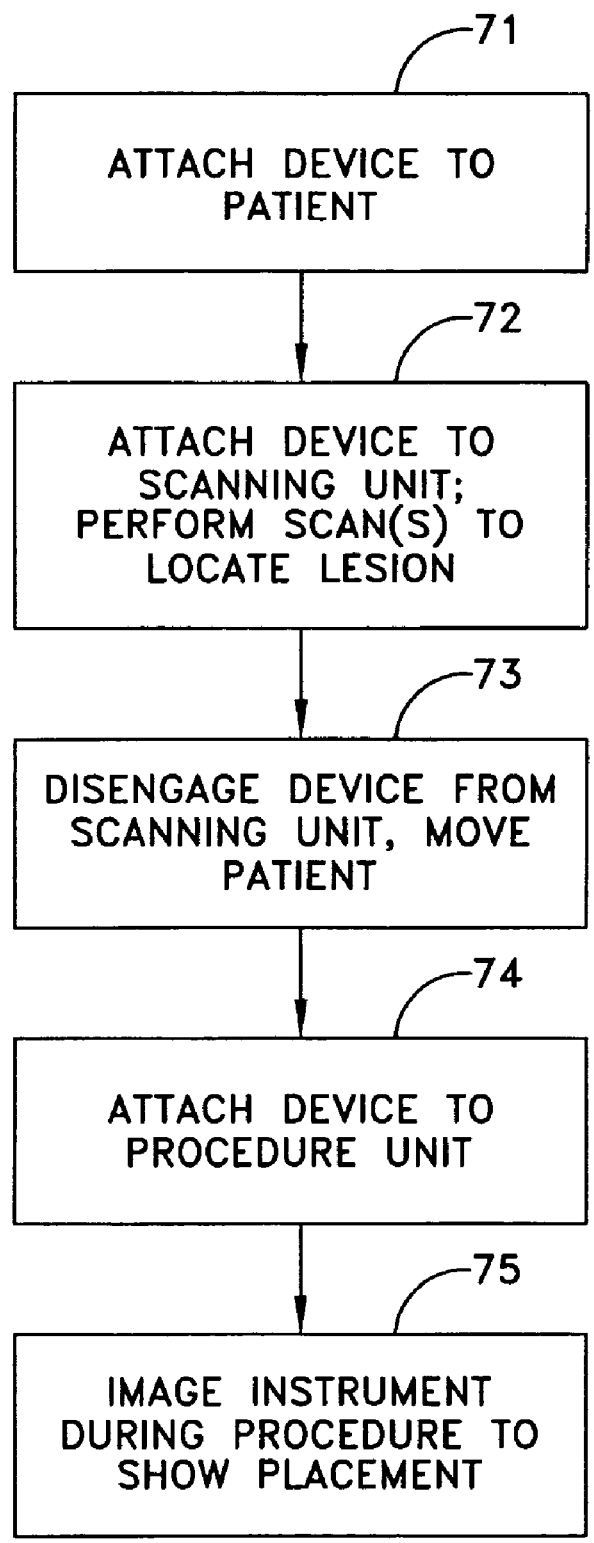
FIG. 7 is one embodiment of a method for performing a medical procedure using an immobilization device.

FIG. 7 illustrates one embodiment of such a procedure.

According to this embodiment, at step 71, an immobilization device is attached to the patient. As described, the immobilization device may be attached to a breast for performance of a medical procedure, such as a biopsy on a lesion.

At step 72, the immobilization device is attached to a scanning unit. This may be done using an interface on the immobilization device adapted to be attached to the scanning unit. One or more scans may then be performed to locate a lesion within the breast.

At step 73 the device may be disengaged from the scanning unit and the patient may be moved. As described above, the medical procedure may then be performed on the patient in a different location.

According to the embodiment shown in FIG. 7, the device is attached at step 74, to a procedure unit. The procedure unit may simply be a fixture that prevents movement of the immobilization device during the medical procedure, to reduce the risk of patient movement adversely affecting the procedure.

In another embodiment, the procedure unit may include an interface permitting imaging of the medical procedure, or use automated control tools, as described above with reference to FIG. 6. Thus, at step 75, the medical procedure may be performed with reference to an image being displayed in coordination with the immobilization device as attached to a procedure unit.

One application suited for this particular type of surgery would be an in-office biopsy.

As described above, the immobilization device may be attached to the patient using a harness or other mechanism. According to certain embodiments, the immobilization device may also be fitted onto an ambulatory device such as a wheelchair, to further reduce the risk of movement of the breast with respect to the immobilization device between scanning and procedure.

In another embodiment, markings may be placed on the breast or other soft tissue to confirm that the tissue has not moved with respect to the immobilization device. For example, one or more openings may be included on the device for this purpose. Once the immobilization device is fitted to the patient, a medical practitioner could use a marker to outline or fill in (for example) a circular opening. If this is done in one or more places on the immobilization device, one can look at the opening and see if that portion of the tissue moved with respect to the immobilization device. If so, the medical practitioner can detect the risk that the position of the immobilization device has moved and, therefore, the reference frame for performing the procedure has moved.

In this circumstance, the patient may return for new imaging to reduce the risk of lesion movement affecting the outcome of the procedure. In alternative circumstances, however, the amount of movement of the device with respect to the soft tissue can be ascertained by examination of the degree of movement of the markers on the breast with reference to the immobilization device, and any change in lesion location determined automatically or manually (e.g., by estimation). This would permit greater accuracy in the performance of the medical procedure when a new image is not taken, would permit confirmation that the immobilization device has not moved, and can increase the confidence and likelihood that the medical procedure will be performed on the appropriate location in the tissue.

In some circumstances, such as where the imaging is being done remotely in time or place from the medical procedure, it may be necessary or desirable to remove the immobilization device. Removal of the device can create risk that the lesion will move and can make it more difficult to locate a lesion within the breast over time. It also makes it more difficult to track changes of the internal structure of the soft tissue over time.

Toward this end, if permanent or semi-permanent markings are placed on the breast with reference to the immobilization device in one or more positions, the device can be attached again to the patient in a manner which reduces the risk that the immobilization device is positioned differently than before.

As can be appreciated, one or more of the inventions described herein can be applied in a number of other applications. These applications include therapeutic implantations, where one or more devices capable of delivering chemicals, radiation or other therapeutic modalities are implanted in the body. Another application would include a sentinel node biopsy. In a sentinel node biopsy, a radioactive or other trackable dye is injected into the target site prior to the biopsy. The techniques described herein can be used, during such procedures, both for positioning of the sentinel node and/or for tracking of the procedure being performed.

In other embodiments of the present inventions, the tools and techniques disclosed herein can be used for diagnostic and historical tracking purposes. Thus, if the immobilization device is used during routine screening mammograms (or any other regularly performed series of scans), the appropriate images may be stored in a database and tracked by patient and time of diagnostic. In the alternative or in addition, certain parameters can be ascertained from each scan and stored. For example, the volume of the breast or a medical anomaly within the breast, e.g., the lesion, may be tracked over time, so that changes in volume can be determined. Marker locations may also be stored.

In one embodiment, temperature sensors and/or heating/cooling elements can be applied in this context. This can be done to assure that, at the time that the volume measurement is being made, the tissue is at the same approximate temperature.

As one might appreciate, certain adjustments might be made to the immobilization device illustrated in FIG. 2 to allow more accurate volume measurements to be taken. For example, for this (and certain other applications) it may be desirable to have a closing surface on the immobilization device (e.g., an end wall), so that the chest, sides of the immobilization device and closing surface form a three dimensional enclosed space.

Where historical patient information is being tracked, different images may be overlaid and changes in the internal image structure may be tracked.

As described above, markers or other mechanisms may be used to assure that the immobilization device is positioned as closely as possible each time, with respect to the breast. Even when such markers are not employed, use of the immobilization device can assist in more uniform imaging of the breast. Thus, for example, using a consistent interface between the immobilization device and the scanning unit may allow more uniform imaging angles over time.

In other embodiments, the immobilization device includes radio opaque markings, or other types of markings which will be visible on the digital image. A computer system may then use these images of the radio opaque markings to assist in correlation of images taken at separate points and time.

In other embodiments, the immobilization device can facilitate multimodal imaging correlation. For these, the immobilization device may be adapted to be mounted to more than one medical imaging device. This can be done using the same or different interfaces built into the immobilization device to attach to the different types of imaging equipment. In an alternative embodiment, the immobilization device has an interface that permits an adapter to be mounted to it. An appropriate adapter may then be selected or configured for each of the different types of imaging equipment that may be used with the immobilization device.

Where an immobilization device is used with different forms of scanning, use of the immobilization device can assist in overlaying of the different images taken. This can be done in one (or both) of at least two ways. First, by having a common frame of reference using the immobilization device, the relative angles and orientation of the scans may be determined fairly reliably in advance. (As described above, markers may also be used to assure that there is no movement of the tissue with respect to the immobilization device between scans.) Since the relative scanning positions of all of the images may be known in advance in this fashion, correlation of the images may be produced more readily.

In other embodiments, radio opaque (or other visible) markings on the immobilization device can be used manually or by computer software to correlate images.

In other embodiments, these types of images whether taken from multimodal sources or multiple scans of a singular source may be used to construct a three-dimensional image or model on a computer screen. One may also be constructed using three-dimensional modeling techniques, in an automated fashion.

In another embodiment of the present invention, the devices may be used to assist in therapeutic radiological planning. In these embodiments, using historical tracking of volume, an internal structure of the breast can be used to better plan and focus application of an external beam, permitting more accurate planning of a cone for a lesion to be irradiated.

Figure 8:
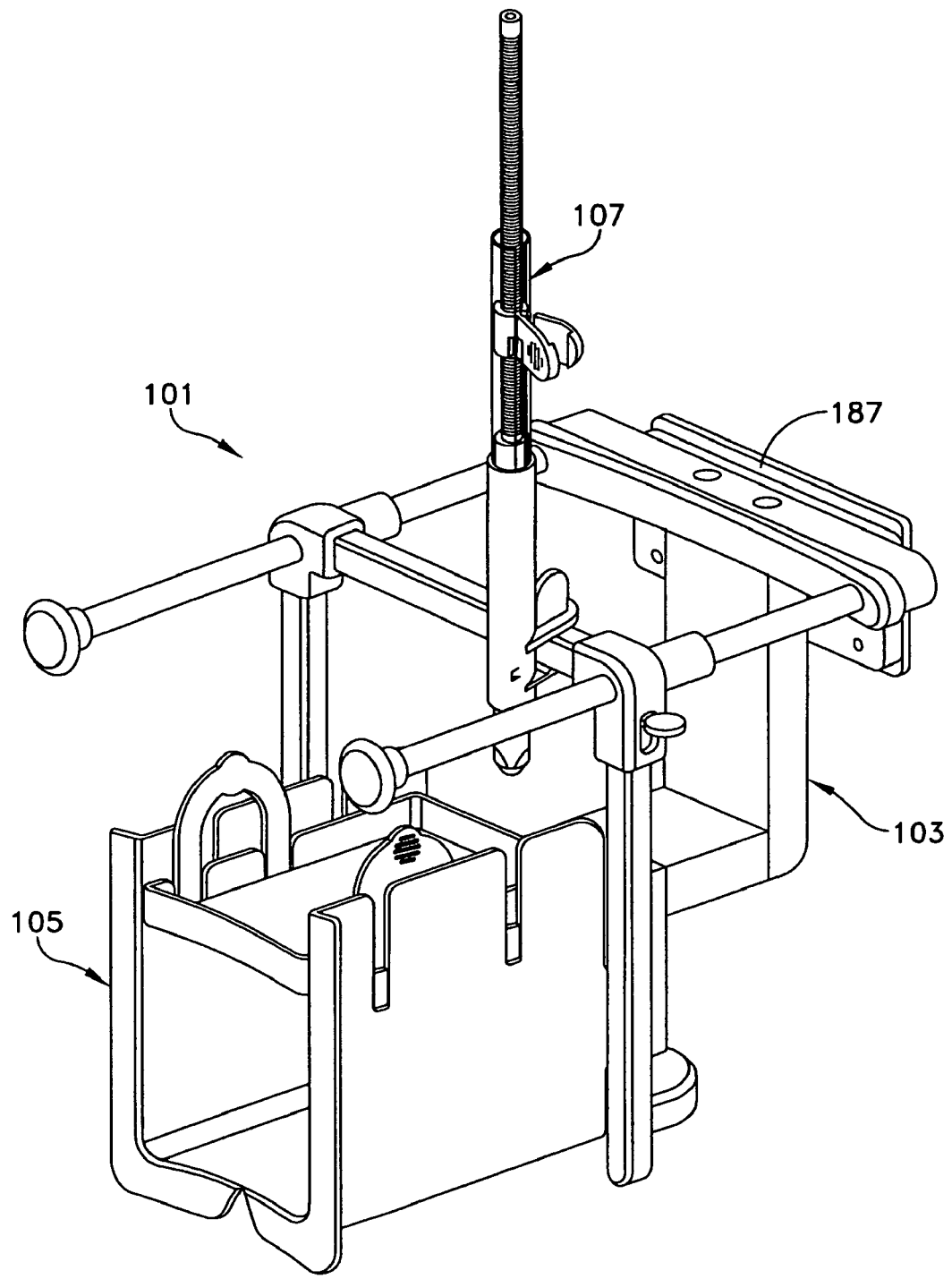
FIG. 8 is a perspective view of another embodiment of a tissue immobilization device.
Figure 8A:
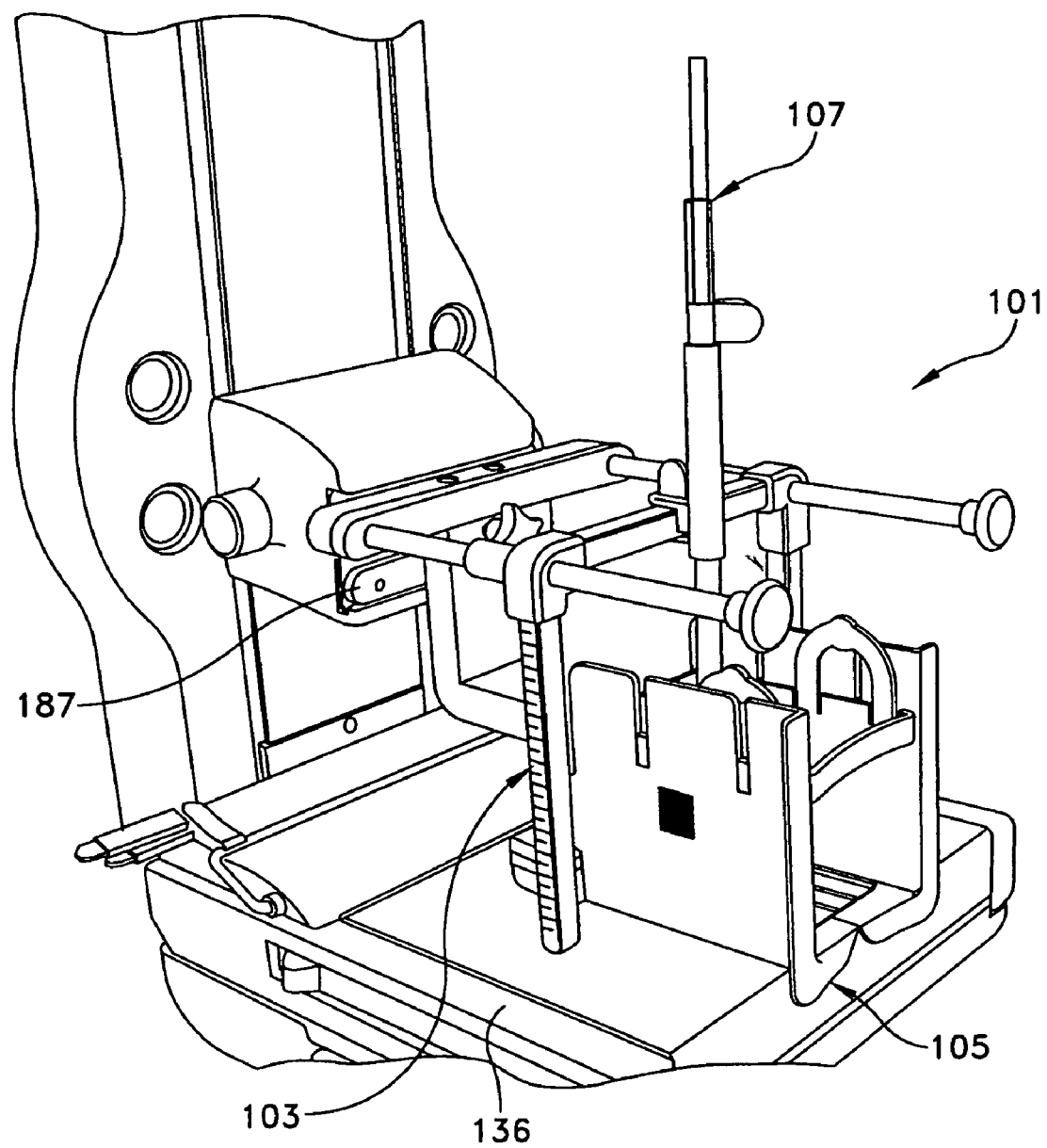
FIG. 8A is a perspective view of the tissue immobilization device shown in FIG. 8 attached to a mammography machine.
Figure 8B:
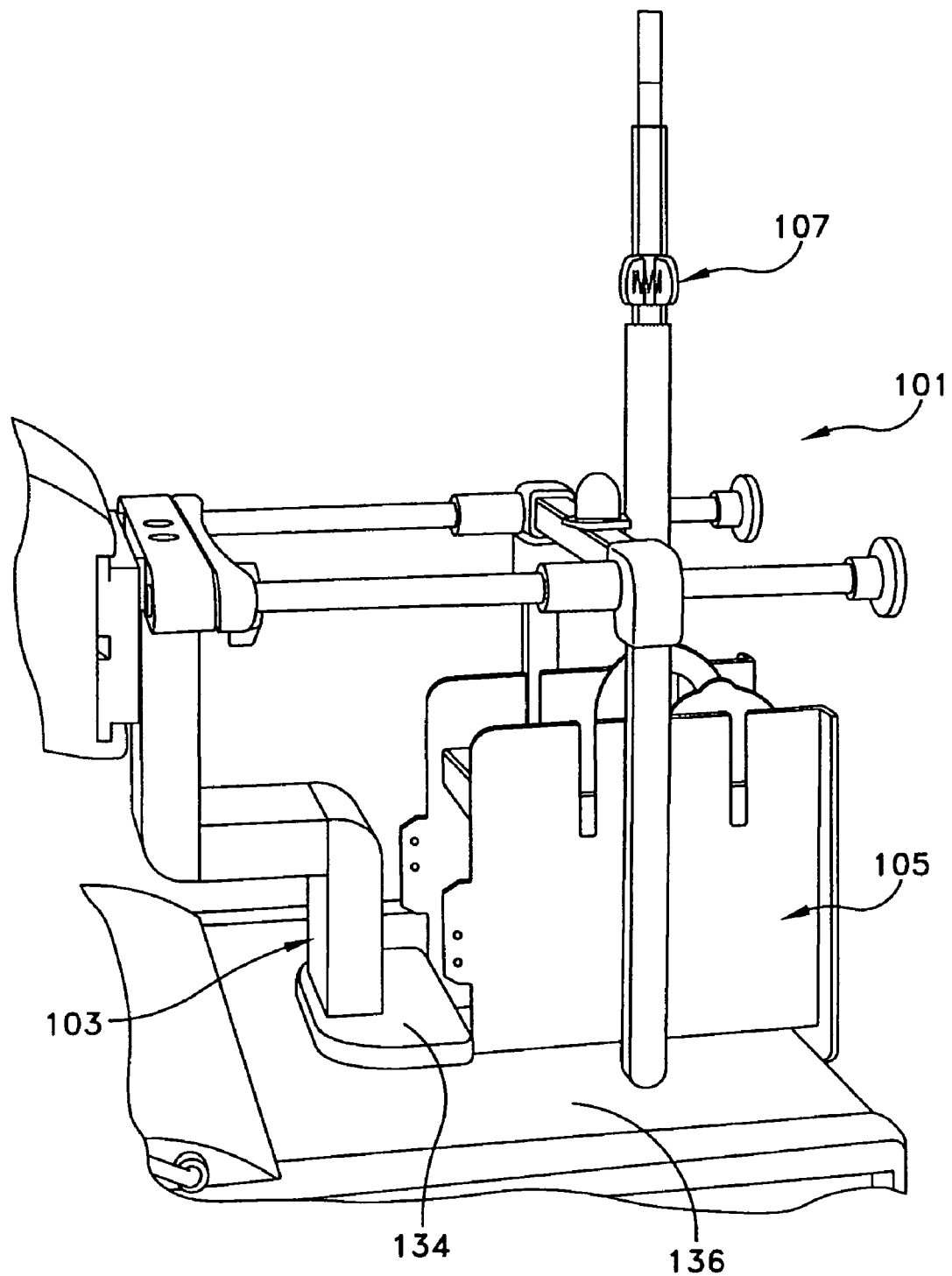
FIG. 8B is a perspective view similar to FIG. 8A taken from a different perspective.

Referring now to FIGS. 8-12, and more specifically to FIGS. 8, 8A and 8B, there is generally indicated at 101 an immobilization unit of another embodiment of the inventions. In this example, the immobilization unit is described with respect to use for needle localization in a patient's breast, e.g., a procedure where a needle is placed in the breast so that the tip of the needle is located at or within the area of interest, permitting another procedure (e.g., a biopsy) to be performed later at that location. This device is suitable, however, for other forms of localization, such as placement of a marker or injection of a dye and is suitable for other procedures such as direct placement of a biopsy needle within the breast. A biopsy gun containing a biopsy needle or some other suitable attachment can also be employed.

The immobilization unit 101, as with device 20, is suitable, for example, for use in performing medical procedures on tissue requiring immobilization, such as taking a biopsy of a lesion within a breast or placing a guide wire in association with performing another medical procedure such as a biopsy. The assembly 105 may be less bulky than device 20, and fabricated from lightweight materials to reduce the device's overall weight. Possible materials include (but are not limited to) plastics such as a polycarbonate, a polyethylene or a polypropylene, semi-rigid or rigid rubbers, light-weight metals and other materials that could be readily selected by one of skill in the art based on the disclosure provided herein. As shown, the unit 101 includes a frame assembly, generally indicated at 103, a tissue immobilization assembly, generally indicated at 105, and a needle assembly, generally indicated at 107. In some embodiments, the frame assembly may be made of a metal, for a more rigid configuration. As one example, though, other assemblies may be attached to the frame assembly for different procedures. For example, an interface may be provided to allow attachment of a biopsy gun to the frame.

The term "immobilization device," as used herein may refer to a device for immobilizing tissue and may include a device that permits adjustment of shape breast between images or during the procedure (as well as those that do not), or an immobilization assembly with or without a frame.

Figure 9:
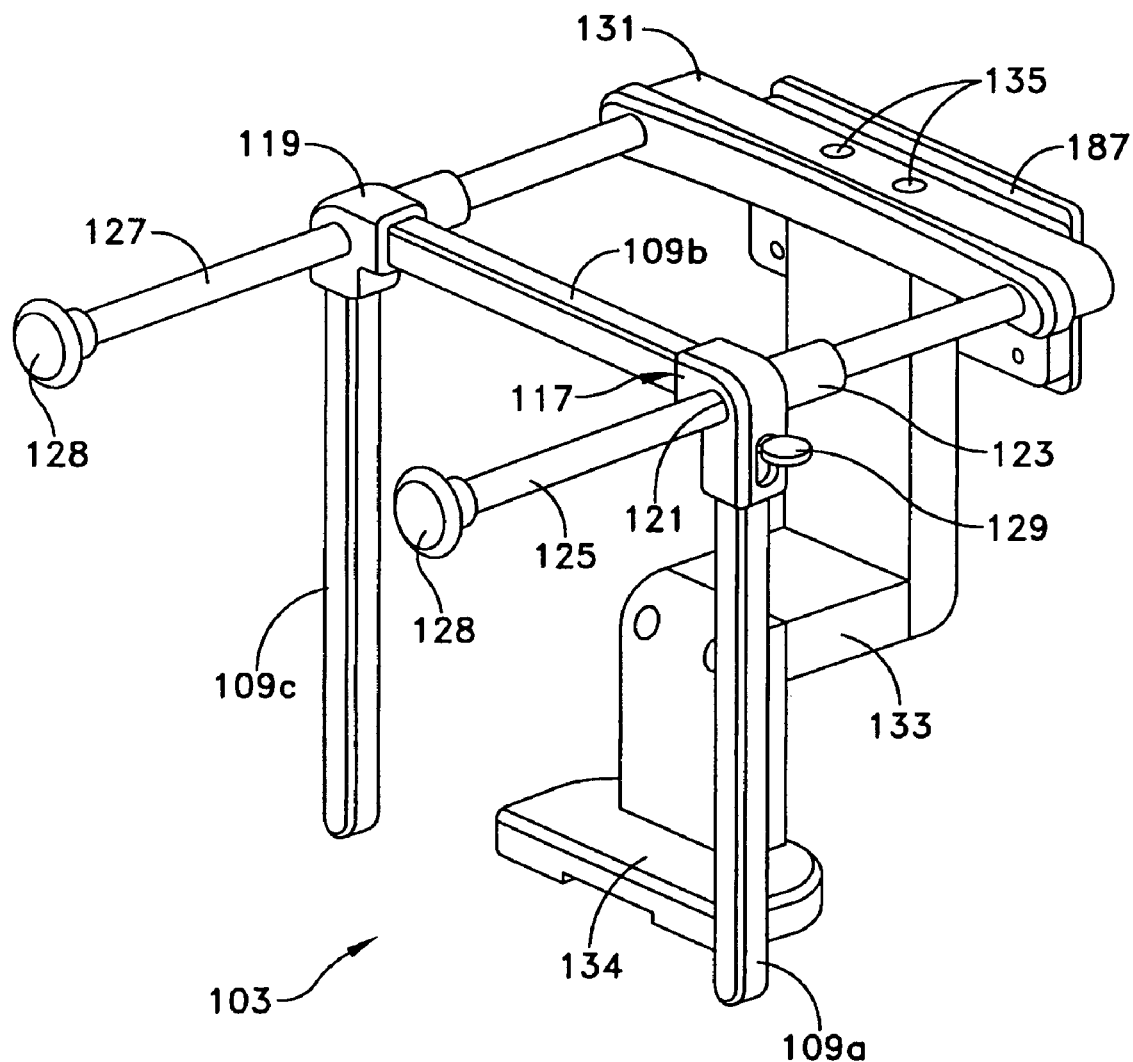
FIG. 9 is a perspective view of a frame assembly of the device illustrated in FIG. 8.

Turning to FIG. 9, the frame assembly 103 is constructed to support the immobilization assembly 105 and the needle assembly 107. The frame assembly 103 includes an inverted U-shaped frame member fabricated from three lengths of stock material, indicated at 109a, 109b and 109c, e.g., light-weight aluminum or an aluminum alloy, plastic, or some other suitable polymeric material, connected to one another by a pair of elbow connectors 117, 119. With reference to connector 117, the connector has an opening 121 formed therein, which extends through a boss 123 formed on the connector. As shown, two rods 125, 127 are received within respective openings of the connectors 117, 119, each opening being sized to receive the rod therethrough. Knobs 128, made of a softer material, are included on the end of rods 125, 127 for the comfort of a patient, should she lean forward into the ends of those rods. For each connector 117, 119, a locking mechanism is further provided for securing the rod in place. Specifically, each locking mechanism includes an outwardly projecting tab 129 adapted to be pressed downward to release the rod 125, 127 from the connector 117, 119. In its pressed, unlocked position, the rod can be axially slid to its desired position. When released, the rod is locked in place by any suitable device contained within the locking mechanism.

The rods 125, 127 may include indicia on each in order to precisely position the U-shaped frame along one axis with reference to an immobilization device attached to the frame portions 109a, 109b and 109c. Since (in this embodiment) the needle assemble 107 is attached to the U-shaped frame, positing the U-shaped frame will precisely position the needle assembly along one axis, with reference to a breast in the immobilization device. In an embodiment described below, a computer, PDA or other device may calculate a position for location of the U-shaped frame for performance of the procedure, and the output specifying where to place a needle (107 in FIG. 8) may then include a reference to where along the rods 125, 127 the U-shaped member 109a-109c should be positioned with reference to the indicia on rods 125, 127.

For a similar reason, the frame parts 109a, 109b and 109c may include indicia calibrated to allow the needle assembly 107 to be positioned along the length of that axis. Thus, by positioning the U-shaped frame 109a-c along one axis and the needle assembly 107 on one of the bars 109a-c, the needle procedure can be specified along 2 axes. By controlling the insertion depth, a point may be determined in a three-dimensional space. As one might appreciate based on the disclosure provided herein, other mechanisms could be adapted to specify and control a point in 3-dimensional space. For example, whether or not a circular immobilization device is used, polar coordinates could be used to precisely specify needle position and the mechanisms designed appropriately.

A horizontally disposed bar 131 secures the ends of the rods 125, 127 to a seat 133. As shown, the seat bar 133 is suitably secured by a pair of fasteners, such as machine screws, to the bar 131. The seat bar 133 extends downwardly from the bar 131, and in this embodiment is "S" shaped. In another embodiment, the seat-bar 133 may be L-shaped. This may be done, for example, to allow more room for a patient's breast that is compressed and extending out of the end of immobilization device 105. As shown, the seat 133 of the frame assembly 103 is adapted to secure the immobilization assembly 105 thereto in a manner that precisely registers the immobilization device with reference to the frame assembly 103 and, since the frame assembly is coupled to the mammography machine and bucky, also with respect to the machine.

In this example, the bottom of the seat bar 133 has tab seat 134. The tab seat 134 (as well as the bottom U-shaped frame member parts 109a and 109c, for purposes of stability) are designed to rest precisely on top of a bucky 136 of a mammography machine when interface plate 187 is attached to the frame assembly 103 and a mammography machine (see FIGS. 8A and 8B). Multiple forms of interface plate 187 (or other mechanism) can be supplied, each adapted to permit a common frame assembly 103 to be attached to different machines.

A tab (not shown) on a immobilization device can be inserted into a slot formed by an opening in the bottom of tab seat 134 and the bucky 136. The tab and tab seat 134 may be formed to assist in proper registration, for example by having a ball bearing in the tab and a corresponding depression in tab seat. The tabs may be removable to quickly disengage the immobilization assembly from the frame assembly.

The frame assembly 103 of the immobilization unit 101 may include a suitable mechanism to permit it to be attached to various medical equipment. For example, the frame assembly 103 could be provided in an appropriate configuration to permit the immobilization unit 101 to be attached to an x-ray imaging system using interface plate 187 and configured so that the bottom of rods 109a and 109c, and the tab seat 134 rest on the bucky 136 when it is so attached. Additional mechanisms could be provided to permit the immobilization unit 101 to interface to different types of equipment, such as other types of imaging equipment, as well as surgical equipment.

By allowing the immobilization unit 101 to be removably connectable to different medical equipment, the immobilization device can be connected to an apparatus for screening, and connected to a separate apparatus for performing a procedure, such as a biopsy. An interface that allows mechanical or automated control to coordinate any procedures may be further provided.

In addition, when the bucky 136 on a mammography machine is rotated to take (for example) a second image from the side, the frame assembly would also be rotated. Since the immobilization unit 101 can be detached from the assembly, this rotation can be straightforward. For example, the immobilization device can be removed from the assembly frame, the bucky (and frame) rotated and then the immobilization device attached again (using a different tab, as described below).

Figure 10:
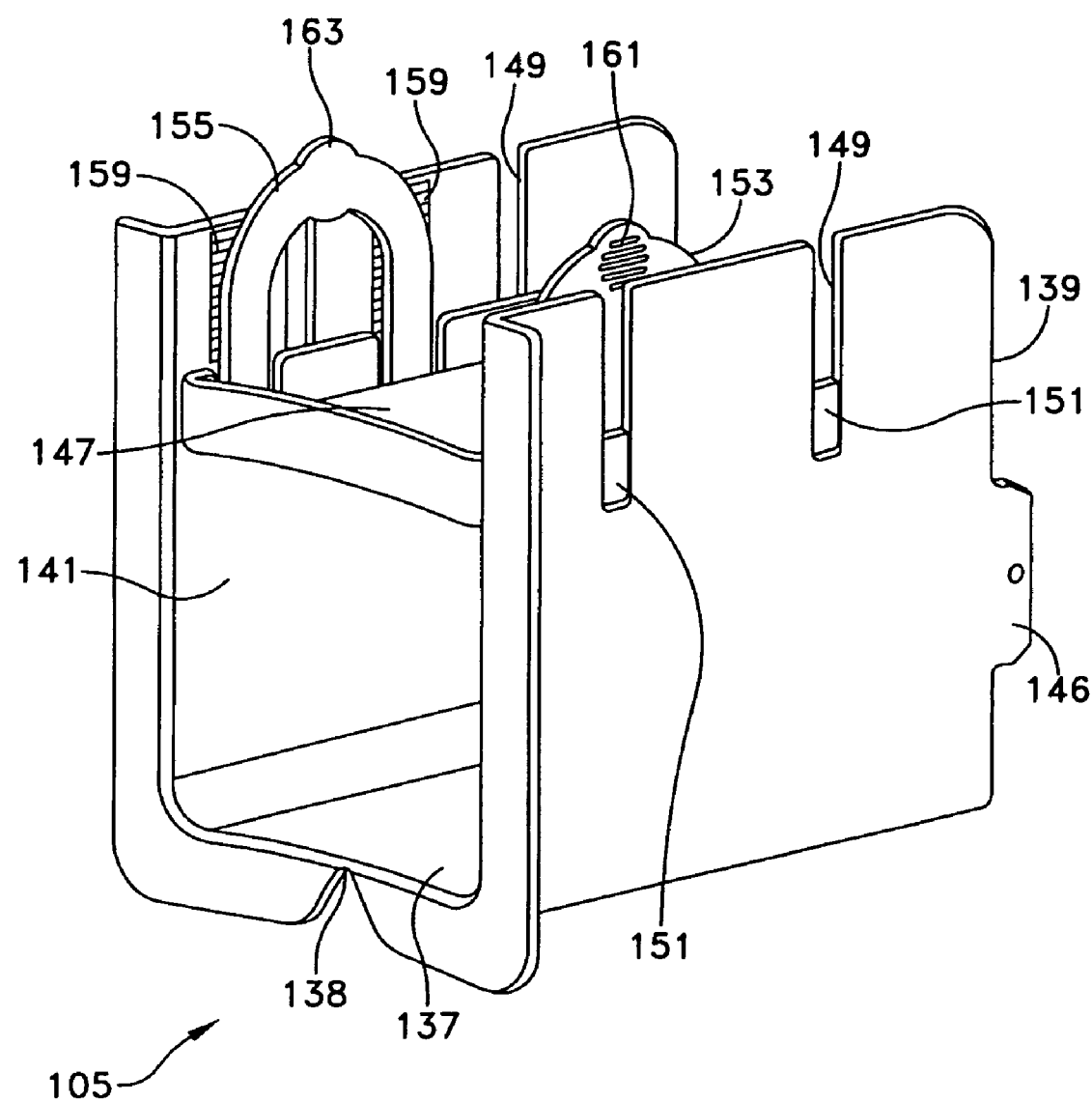
FIG. 10 is a perspective view of an immobilization assembly of the device illustrated in FIG. 8.

Referring to FIG. 10, the immobilization assembly 105 of this example is generally square shaped in construction to receive the tissue to be immobilized, e.g., a breast. In this example, the top piece 147 is curved. In this example, compression is achieved by pushing down on the top piece as described below.

The immobilization assembly 105 includes a bottom wall 137 and two side walls 139, 141 integrally formed with the bottom wall. The bottom and side walls 137, 139, 141 are sized to receive the tissue to be immobilized. The immobilization assembly 105 may be sized appropriately for compression of a breast. As breast sizes vary, it may be desirable to provide more than one standard size, e.g., correlating size to breast or bra size. As shown, the interior surfaces formed by the bottom and side walls 137, 139, 141 are smooth to reduce the risk of pinching the tissue during operation of the unit 101.

With reference to FIGS. 8A and 8B, in addition to FIG. 10, each side wall 139, 141 has a tab portion 146 formed at the rear of the side wall 137 or 139 and also on the bottom (not shown in these drawing figures). As described above, the tab portion may be secured to the tab seat 134 of the frame assembly 103 by a suitable fastening method. By including a tab portion on the bottom and each side, a top, left or right side view may be taken by rotating the bucky of a mammography machine (with a frame assembly 103 attached) and then using the corresponding tab portion with tab seat 134 to secure and register the device to the machine.

Each of the tab portions may further include a corresponding radio-opaque marking. This would permit someone reading an X-ray to readily ascertain which view was taken.

The immobilization assembly 105 further includes a top wall 147 slidably connected to the side walls 139, 141. Specifically, at the top of each side wall 139, 141, two vertical slots, each indicated at 149, are formed therein. Each slot 149 is adapted to receive a positioning detent, each indicated at 151, which is formed along an edge of the top wall. The top wall 147 is secured in place by two inverted U-shaped members 153, 155, each member being positioned adjacent a respective side wall 139, 141 and formed with the top wall so that it projects perpendicularly from the top wall. The outwardly facing surface of each inverted U-shaped member 153, 155 has a serrated area (not shown) adapted to mate with a serrated area 159 formed on the respective inner facing surface of its respective side wall 139, 141 to secure the top wall 147 in place with respect to the side walls. By applying inwardly directed pressure to each member at 161, 163, the serrated areas of the members 153, 155 disengage their respective serrated areas 159 of the side walls 139, 141 to enable the top wall 147 to move up and down between the two side walls with the detents 151 sliding in their respective slots 149.

The arrangement is such that upon placing tissue within the immobilization assembly 105, e.g., breast tissue, downward pressure can be applied to the tissue by moving the top wall 147 downwardly within the assembly. The serrated areas, once the top wall 147 is positioned to secure and immobilize the tissue, retain the top wall in place with respect to the side walls 139, 141 to maintain pressure on the tissue. As shown, the inwardly facing surface of the top wall that engages the tissue is slightly arced to provide additional comfort to the patient.

By sizing the immobilization device appropriately, one can appreciate that the downward pressure on the top result in compression of the breast along two dimensions. In some embodiments, immobilization assembly 105 may be provided in standard sizes intended correlate to breast size, such as cup size of the breast and an appropriate sized unit selected for the particular patient.

It should be understood that although the top wall has four such positioning detents 151 received within four slots 149, any number of detents and slots can be provided for guiding the top wall 147 with respect to the side walls 139, 141 to immobilize the tissue and other suitable securing mechanisms can also be readily designed based on the disclosure herein. In addition, although the side walls 139, 141 shown in FIG. 10 have slots 149 that extend down from the top edge approximately one-third the way down their respective side walls, the slots can extend further down the side walls to further reduce the volume defined by the bottom, side and top walls 137, 139, 141, 147.

The immobilization assembly 105 can be fabricated by any suitable rigid, nonmagnetic and radio-translucent material, for example. In this example, the immobilization assembly 105 is rigid in order to minimize the movement of the soft tissue (e.g., a breast) during the procedure in between scanning and procedures. Softer materials may be used in any context in which the loss of accuracy (if any) caused by permitting additional movement of the breast between scanning and procedure is acceptable. As with device 20, the immobilization assembly 105 of the immobilization unit 101 may be constructed using a semi-rigid material, a flexible material or a combination thereof. In addition, certain soft materials can be used to provide an exterior shell with materials enclosed that have volume-filling properties, such as various gels.

In some embodiments, as a safety measure or to help assure the patient's comfort or to help assure a proper fit, pressure sensors may be used to assure that a sufficient (but not too large) amount of pressure is being applied to compress the breast. An automatic release (or loosening) mechanism may be provided where a pressure threshold is exceeded.

In one embodiment, holes are included in appropriate places in portions of the immobilization device to allow insertion of a needle. The hole may be molded in or drilled and the positioning of the holes may be coordinated to correspond to the calibration markings on the frame assembly.

In this example, the holes may be positioned in the top and each side wall to permit a needle to be inserted from the top or either side since (in this example) a rigid or semi-rigid material completely surrounds the sides of the breast. In this example, and using this embodiment of a frame assembly, insertion of the needle is always made at about a right angle to the surface of the immobilization device. The holes may vary in shape and size in order to accommodate certain medical procedures or instruments. For example, the holes may be constructed to enable the procedure of a "biopsy in a circle" when it is desirable to move the needle with respect to the frame assembly and/or the immobilization assembly. Also, the holes may be configured to accommodate a biopsy gun, which is capable of pivoting about a fixed or movable point on the frame assembly (or the immobilization assembly, as the case may be). The immobilization device may be further configured to interface with other tools for precisely aligning the device with a machine upon which it is attached.

In this example, if holes are not included at the edges of in the immobilization device, and even where they are, it may not be preferable to endeavor to perform a procedure on an area of interest that is near a corner or side of the immobilization device. Where this is the case, the device can be positioned on the patient at an angle. When the device is positioned on a screening device, the patient may then have to angle her body to one side so that the device is fitted squarely into the bucky.

In this embodiment, the immobilization device 105 includes an area of thin material (e.g., scored) along the bottom running from a center of the bottom portion proximal the patient to the center distal end. In this example, this channel permits the device to be broken or snapped apart for quick removal. This channel is not meant to break during use, but instead is intended to hinge apart for quick removal from the patient. For example, the bottom wall 137 may include a crease 138 to enable the bottom wall to hinge apart along an axis defined by the crease upon flexing the side walls 139, 141 apart from each other. The purpose of the crease 138 will be described in greater detail below.

Figure 11:
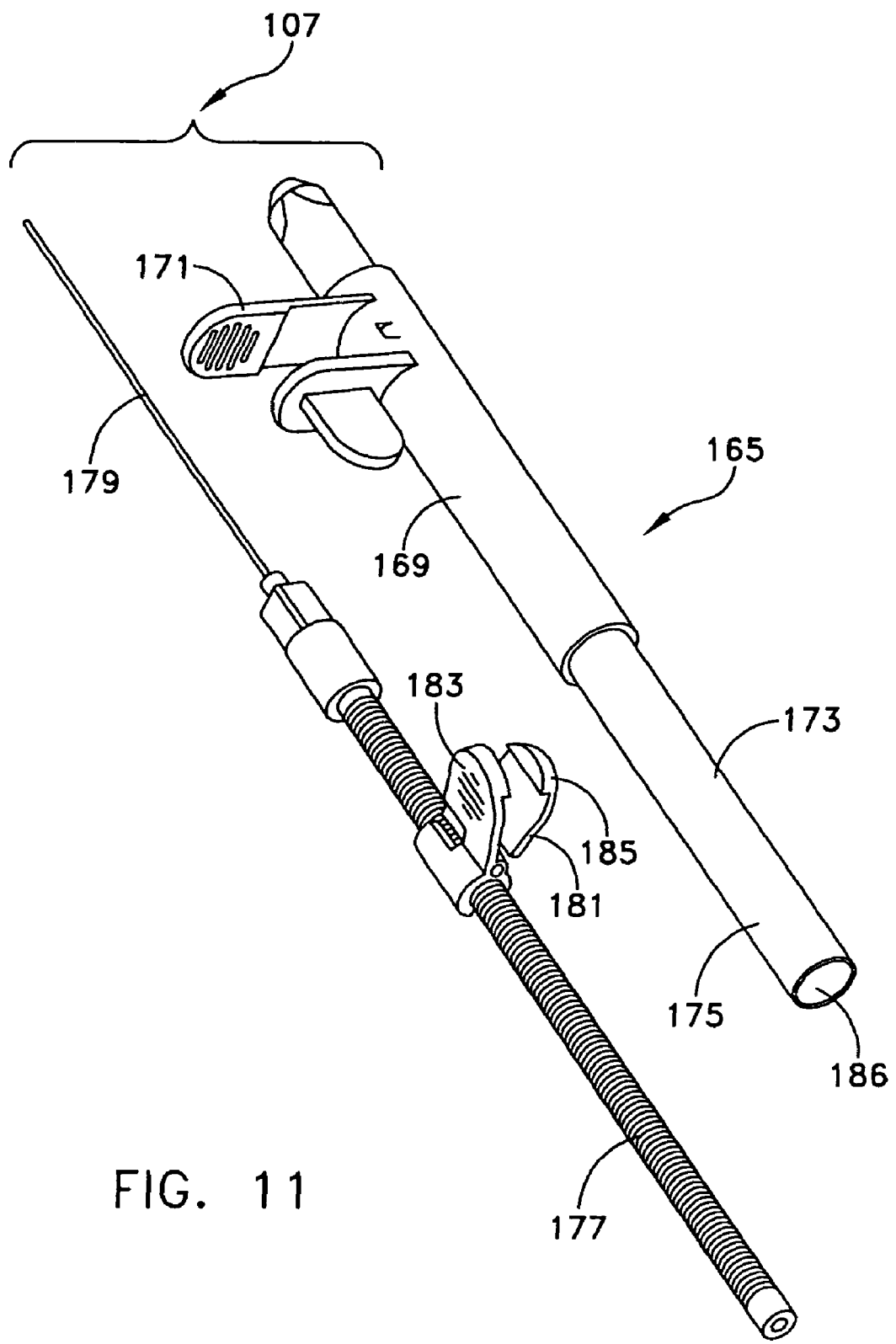
FIG. 11 is a perspective view of a needle assembly of the device illustrated in FIG. 8.

The needle assembly 107 is illustrated in FIG. 11, and comprises a needle holder 165 capable of being secured to the frame assembly 103. As shown, the needle holder 165 includes an sleeve 169 having a clamping assembly 171 configured to permit the needle holder to be securely attached to the frame assembly as described generally above. The clamping assembly 171 should be configured, and a suitable material selected, to avoid play or rocking of the holder during use. Referring back to FIG. 8, the clamping assembly 171 is capable of releasably clamping onto a frame member portion 109a, 109b or 109c to position the needle holder 165 adjacent the immobilization assembly 105.

The needle holder 165 of this example further includes an outer sleeve 173 sized to fit within the sleeve 169 by suitable means. The outer sleeve 173 has internal threads (not shown) formed therein and a longitudinal slot 175 best illustrated in FIG. 11.

The needle assembly further includes a tubular member 177 adapted to be slidably received within the inner sleeve 173. A needle portion 179 suitably secured to the tubular member 177. A pointer etched on the needle portion may be provided to indicate the orientation of the needle opening. The arrangement is such that the tubular member 177 is capable of axially moving with respect to the inner sleeve 173 so that the needle can be inserted through the outer sleeve 173, through a hole in the immobilization device and into the patient to finely position the needle portion 179. The tubular member 177 may also be rotated to assist in achieving the insertion of the needle portion 179 into the tissue.

The tubular member 177 may include calibrated markings along the length of the tubular member. A positioning element or clamp 181 may be secured to the tubular member by pinching a pair of tab portions 183, 185 adapted to be pressed together to unclamp the positioning element and axially move the positioning element with respect to the tubular member. By releasing the tab portions 183, 185, the positioning element 181 is spring-loaded to clamp onto the tubular member 177. To insert a needle, the needle portion 179 and the tubular member 177 are slide into the outer sleeve 173 and down until the positioning element 181 engages a top portion of the outer sleeve. Thus, the positioning of the positioning element 181, with reference to the markings on the tubular member 177 can precisely determine the depth of the insertion of the needle portion 179 into the tissue. As might be appreciated, therefore, the positioning of the U-shaped pieces 109a-c along the rods 125, 127 of the frame assembly, the position of the needle assembly 107 along one of the pieces 109a-c and the insertion depth (determined in this example by the location of the positioning element 181) can specify precisely in three-dimensional space where the tip (or any other part) of the needle portion 179 is positioned.

Still referring to FIG. 11, the outer sleeve 169 and sleeve 173 of the needle holder 165 may be formed with a crease 186 to flex the needle portion along an axis defined by the crease upon spreading apart the outer sleeve and the sleeve via slot 175. This construction enables the needle holder 165 to be removed from the tubular member 177 and needle portion 179 without removing the needle from the tissue.

The immobilization unit 101 may include a mechanism to permit it to be attached to various medical equipment, as described above. For example, a plate 187 (see FIGS. 8, 8A, 8B and 9) secured to the horizontal bar 131 could be provided in an appropriate configuration to permit the immobilization unit 101 to be attached to an x-ray imaging system or a mammography machine, for example. This would permit the unit 101, and therefore the breast, to be more accurately and reproducibly positioned with respect to the x-ray equipment. Additional mechanisms could be provided to permit the immobilization device to interface to the same equipment supplied by a different manufacturer, different types of equipment, such as other types of imaging equipment, as well as surgical equipment.

In addition, the immobilization assembly 105 can be removed from the immobilization tissue prior to performing the procedure by removing the top wall 147 (by pinching members 153, 155), and lifting the top wall away from the side walls 139, 141. For example, if the needle is inserted through an opening in a side wall (e.g., side wall 139) as described above, the other side wall (e.g., side wall 141) can be flexed apart via crease 138 in the bottom wall 137. Once the side wall (e.g., side wall 141) and one-half the bottom wall 137 are moved away from the immobilized tissue, the other side wall (e.g., side wall 139) can be removed by slipping the wall over the needle and/or marker.

By allowing the immobilization unit 101 to be removably connectable to different medical equipment, the immobilization device can be connected to a device for screening and connected to a separate device for performing a procedure such as a biopsy. The provision of an interface allows mechanical or automated control to coordinate any procedures since the frame of reference or each materials is known.

The immobilization unit 101 may include an interface unit (not shown), similar to the interface unit 26 for immobilization device, for control of the device. For example, the unit 101 may be equipped to sense pressure on the walls of the device, as a safety measure to ascertain how hard a device is squeezing the tissue. This may be done by incorporating sensors into the immobilization unit 101. In the alternative, a liner may be used with the immobilization unit 101 which can assist with sterilization and comfort. If so, in some embodiments of the invention, pressure sensing devices could then be incorporated in the liner. The interface may further include a mechanism to automate the control of the movement of the top wall of the immobilization unit 101.

The immobilization unit 101 may also have heating and/or cooling elements built into the device, or incorporated into a liner for use with the device. Where this is done, the heating and cooling of the tissue within the immobilization unit 101 may also be controlled through an interface. In some embodiments, temperature sensors may also be incorporated, to monitor the temperature of the tissue. A feedback loop may be formed to control heating and/or cooling of the tissue to maintain an appropriate temperature for either comfort or the particular medical procedure being performed.

Whether used in conjunction with sensors (such as pressure or temperature sensors), a liner may be provided for use with-the immobilization unit 101. Such a liner may be shaped for use in connection with immobilization unit 101 and may be sterilized where a surgical procedure is being performed. Such liners may be provided, and pre-sterilized, in packaged separate units.

In another embodiment, the immobilization device and needle assembly may be packaged as a pre-sterilized kit or separate kits. Such a kit may be intended to be disposable after a single use.

In other embodiments (or this one), the immobilization unit 101 may be made of a lightweight material in some embodiments, to make the device easier to hold in place when supported by the patient and to reduce discomfort. As one example, a variety of thermoplastic material, such as Lexan may be used to fabricate the immobilization assembly 105, and a lightweight alloy may be used to fabricate the frame assembly 103. (While the term "assembly" is used to describe various components of embodiments of the present invention, this term is intended to include an integrally formed component that is not actually assembled.)

Figure 12:
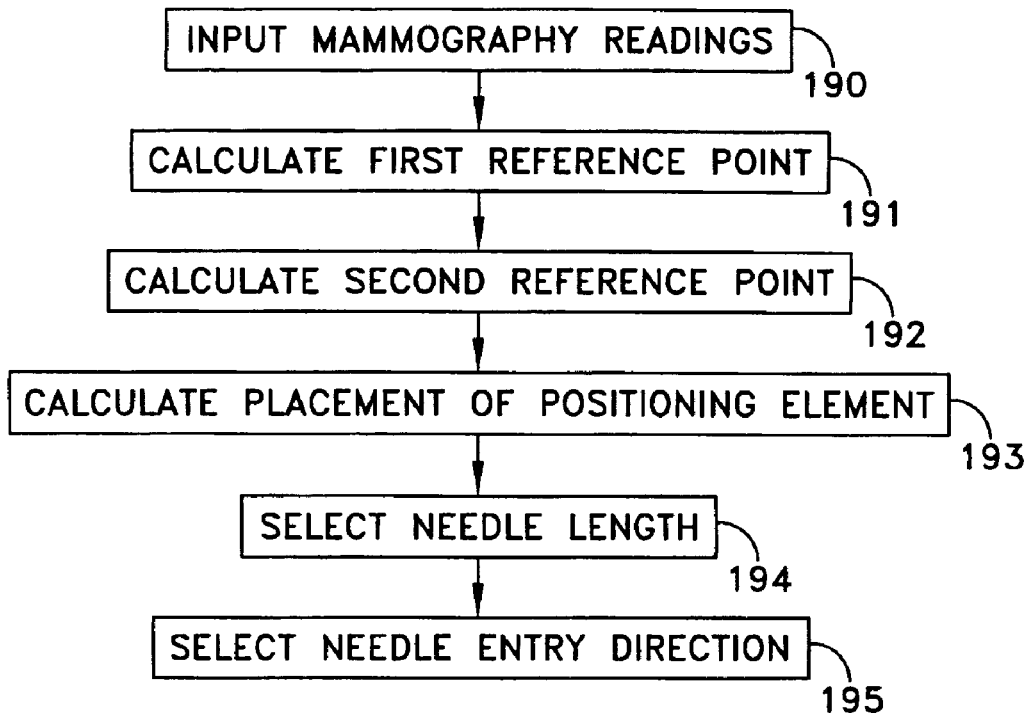
FIG. 12 is an embodiment of a method of calculating reference points for positioning a needle assembly.

Turning now to FIGS. 12-22, and more particularly to FIG. 12, a method according to an embodiment of the inventions for using the immobilization device is further described. In this example, and with reference to FIG. 12, the immobilization unit 101 is used to perform needle localization. Mammography readings from two directions are taken and the results input to a PDA (step 190). The PDA then calculates a reference point on the frame assembly, e.g., a posterior-anterior position along the rods 125, 127 for the frame member (step 191), the medial-lateral position on the appropriate portion of the frame assembly portions 109a, 109b or 109c (step 192), and the location for placement of the positioning element 181 on the tubular member 177 (step 193), to fix the depth of insertion. These calculations are based on information inputted by the technician or appropriate medical practitioner. For example the length of the needle may be inputted or as identified herein selected from a menu of needle lengths (step 194). Also, the needle entry direction may also be inserted (step 195). In one example, the reference markings on 109a, 109b and 109c may have different designations, so that the user is reminded during the procedure to place the needle assembly 107 on the correct portion 109a, 109b or 109c. Similarly, the reference markings on each of the other elements (rods 125, 127 and the tubular member 177) may be different to reduce the change that a user may transpose designations when performing the procedure.

Figure 12A:
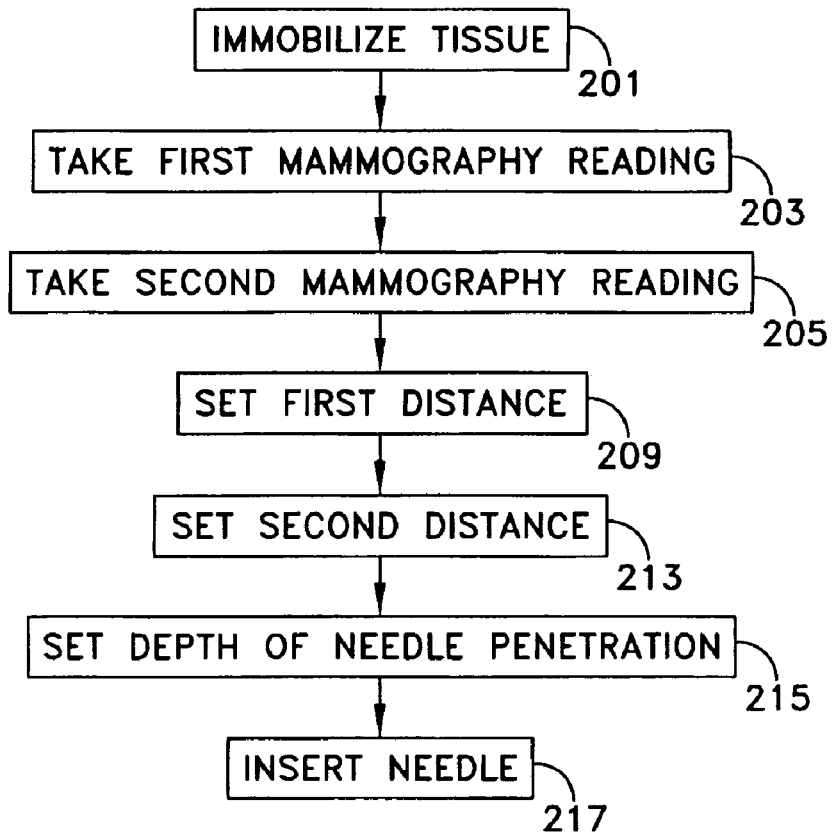
FIG. 12A is an embodiment of a method of performing a medical procedure on soft tissue, using the embodiment of FIG. 8.

With reference to FIG. 12A, at step 201, an immobilization device, such as those described according to one or more embodiments disclosed herein, is attached to the patient to immobilize the tissue having the target tissue or mass (or a targeted area or area of interest).

In step 203, after the immobilization device is affixed to the patient and, in some embodiments, to a bucky of a mammography machine as depicted in FIGS. 8A and 8B, and described herein, a first mammography reading is taken with respect to one direction (e.g., from the top). At this time or at another time, the reading is input into a computer system having firmware and/or software to perform a calculation of the location of the legion. Such a "computer system" may be any computational device including personal computers, PDAs, or special hardward provided for this purpose. Such a system may allow automated reading of the mammogram or the data may be read by a qualified medical professional. The mammogram reading may be read or input to a computer such as a PDA (of course, automated calculations are not required for use of an immobilization device and are present only in accordance with some aspects of the present inventions).

Figure 13:
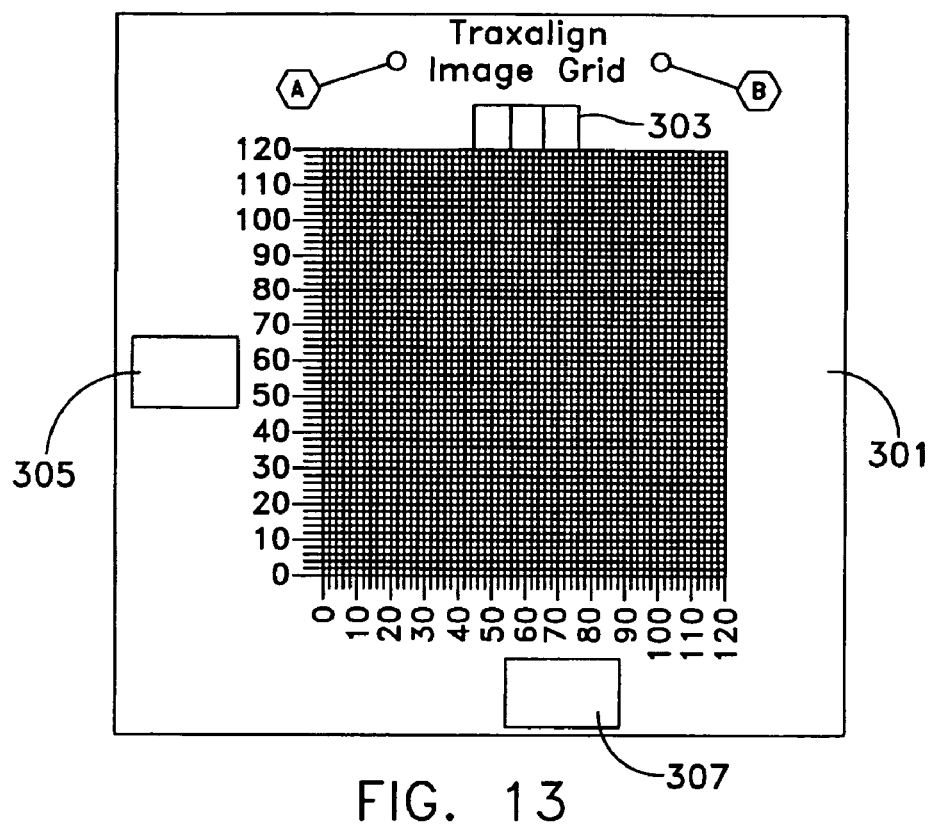
FIG. 13 is a view showing an image grid of an embodiment of the present inventions.

The first mammography reading may be input with reference to an image grid 301, which is illustrated in FIG. 13. Specifically, the direction of the first image is indicated by selecting a "top," "left" or "right" button contained on the image grid 301. As shown, FIG. 13 illustrates the image grid 301 for recording the location of a lesion to be treated.

In addition, radio-opaque reference markings that are on the tab seat 134 of the frame assembly also appear on the mammogram. When the data is input, the data determines the x-y position on the mammogram and, by implication, the x-y position of the lesion (or area of interest) with reference to the immobilization device.

At the top of this grid 301, one of three boxes 303 must be checked to ascertain whether the image corresponds to a top, left or right view. As described above, a radio-opaque marking may be included in each respective tab of the immobilization device to create a radio-opaque marking with a position that corresponds to the location where a user inputs the type of view. For example, a dot may be placed in the tab, creating a dot at the top of the mammogram, where the location of the dot in the tab and mammogram is in the center (for a top view), left of center (left view) or right of center (right view).

At the left side of the display, a user may input into a box 305 the Y coordinate as read by a medical professional. At the bottom, a user may input into a box 307 the X reading.

At step 205, in some embodiments, the immobilization device is disconnected from the mammogram machine bucky, and the bucky rotated to take a second reading from a different direction (e.g., from the left) and a second mammography reading is taken. The result is input in a similar manner as the first mammography reading. As described above, in some embodiments, it may be necessary or desirable to take an asymmetric scan. For example, if the breast of the patient being examined is compressed symmetrically, in some circumstances, it may be possible that a clearer image cannot be taken through the breast, without first reducing the thickness of the tissue through which the x-rays pass. In this circumstance, the immobilization device may be adjusted out of an asymmetric position to permit more than one shape during scanning. Thus, the device may be used to flatten the breast horizontally for a first scan, and then manipulated to flatten the breast vertically for a second scan. In other embodiments, however, the immobilization device is not changed, avoiding movement of the area of interest during the process.

Since the first (e.g., top) reading is in two-dimensions and the second (e.g., side) reading is in two-dimensions, the inputs can be cross-checked to ascertain whether there is an anomaly in the data. If so, the user may be warned and the magnitude of the anomaly calculated and displayed. For example, the software and/or hardware are configured to correct for the effects of parallax. The accuracy of the position of the lesion is dependent on the accuracy of the data provided. The software and/or hardware create two theoretically intersecting vectors based on the data input for the x and y coordinates provided by the use of each image and the know characteristics of the imaging system. If the data points provided are accurate and close to the lesion image on the reading, then it is reasonable to assume the calculations below accurately reflect the three-dimensional location of the lesion within the immobilization device.

Figure 13A:
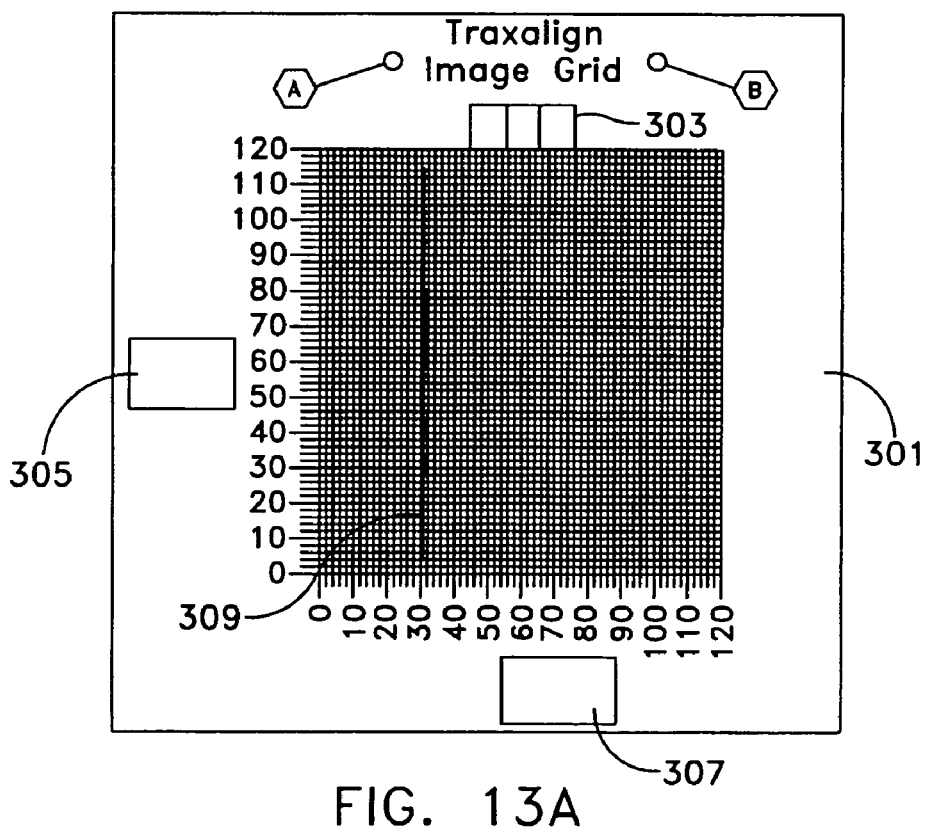
FIG. 13A is a view showing the image grid of FIG. 13 with a first reading plotted on the image grid.

In another embodiment, and with reference to FIG. 13A, when the second reading data is input, a mammogram chart is displayed along with a line on the screen showing where on the mammogram the region should be, to correspond to the data input on the screen. For example, if x-y are input from a reading from the top, the x-reading from the side should correspond to the y-reading from the top. As would be appreciated from the discussion with reference to FIG. 13B below, "corresponds" may not be a one-to-one relationship. That is, where parallax error may be introduced with particular imaging systems, a geometrical calculation may be applied to translate the x-y reading from the top (for example) to a line on a side view showing where on the reading the x-reading should be. As shown in FIG. 13A, line 309 represents the x-reading taken from the first mammography reading. Thus, the position of the lesion should be located along this line 309 after inputting the second reading data, and specifically the y-reading.

Displaying this line can assist a person reading the x-rays in selecting from among multiple possible areas of interest where, for example, multiple lesions exist within a breast or the area of interest is a grouping of many small lesions.

When two sets of data are input (e.g., x-y reading from a top and side view), the correspondence between measurement (for purposes of calculating anomalies or displaying a line) may not be linear. In some imaging equipment, the source of radiation may be a point or fan source. The result may be a distortion of the 2-dimensional image, sometimes referred to as parallax error.

Figure 13B:
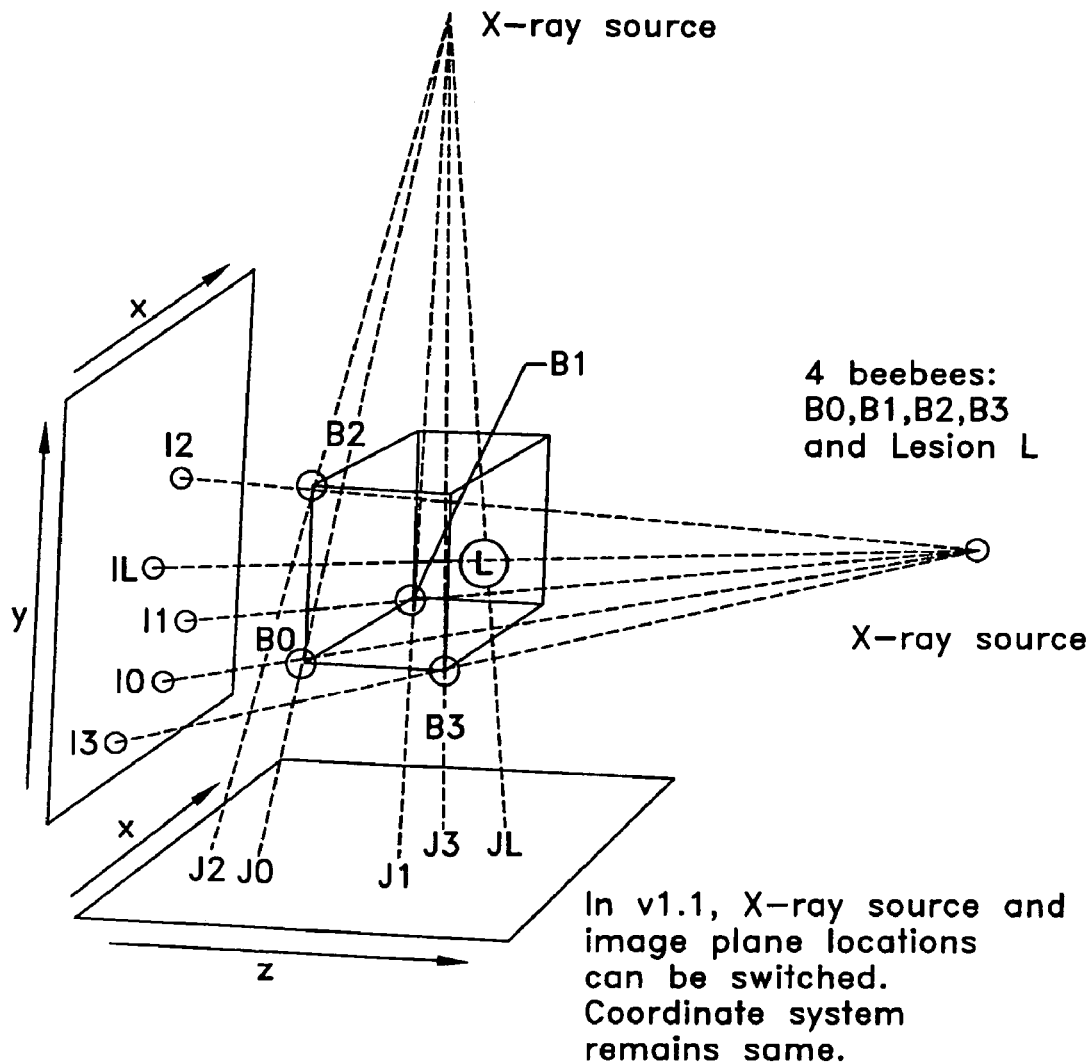
FIG. 13B is a view of a coordinate system illustrating an image taken by two image sources.

This distortion may be corrected or otherwise accounted for, for example, by calibrating the system to a particular imaging device. Specifically, the accuracy of the data can be verified by plotting the distance of the lesion against four known reference points generated by the intersection of the x-ray source along a known plane. As illustrated in FIG. 13B, a beebee labeled B0 is the origin of the coordinate system, e.g., a corner of the immobilization device. The distance from the lateral image plane B0 is assumed to be known and input. The distance from the frontal image plane to B0 is also assumed to be known and input. It is assumed that the other three beebees, beebees B1, B2 and B3, are at locations 0,0,L3, 0,L2,0 and L1,0,0, respectively, all also known. In one embodiment, the four beebees may be provided on the immobilization assembly 105, for example, or on a frame attached to the assembly. In other embodiments, two beebees may be provided on the frame assembly 103, e.g., on tab seat 134. These two beebees are identified by A and B on FIGS. 13A and 13B. It is assumed that the x-ray source is at a distance DL from the image plane in lateral view (positive or negative) and DF from the image plane in frontal view. The location of the lesion should be within the space defined by the four beebees B0, B1, B2 and B3, e.g., when these are at the extremities of the device (although they may also be positioned within the device so long as the lesion is located within the beebees).

After the data has been input, the system has sufficient information to ascertain the degree and form of parallax error for the particular imaging system, and the point in three-dimensional space where a lesion is located, with reference to the immobilization device.

After the degree and form of parallax error has been ascertained, future measurement of parallax error (e.g., measurements of the beebees that define the coordinate system) may not be necessary. Since the immobilization assembly can be registered in the same position each time with respect to the imaging unit, this date would be essentially the same and, therefore, does not have to be measured and input each time. Instead, the system may adjust for parallax error based only on the data input for the lesion. Where this is done, the two-dimensional image still needs to be correlated or registered with respect to the immobilization device. Radio-opaque markings on the immobilization assembly or the frame assembly may serve that purpose, e.g., markings in tab seat 134.

Other methods would for adjusting for possible parallax error in the context of the present inventions could be determined and implemented based on the disclosure provided herein.

Figure 14:
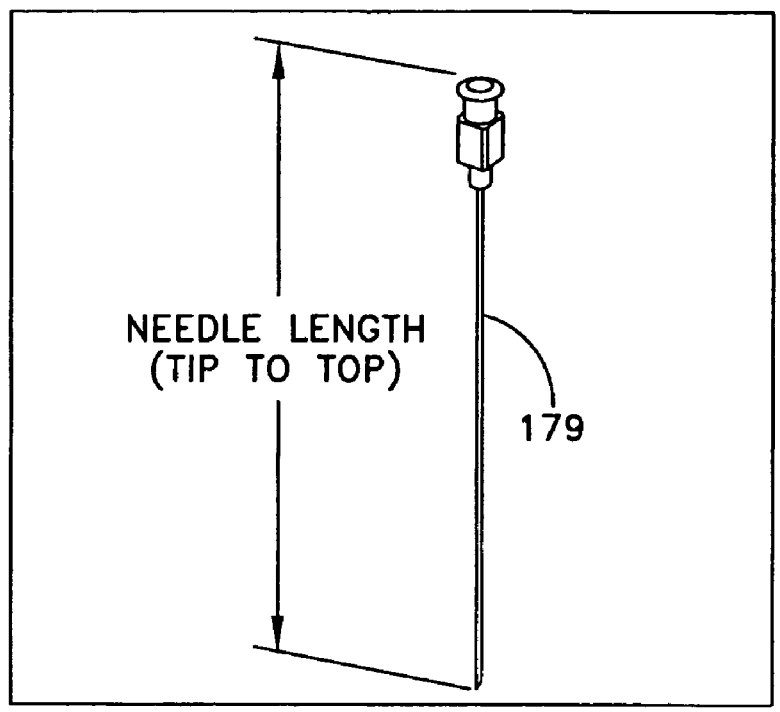
FIG. 14 is a view showing one embodiment of a step of determining a needle length.

Referring again to FIG. 12A, at step 207, and with reference to FIG. 14, the length of the needle portion 179 is taken from the tip of the needle portion to the base of the needle portion that connects to the tubular member 177. Preferably, the length of the needle portion 179 is measured in millimeters. This measurement is input. The system may include a variety of default options for standard needles as well as an opportunity for a user to input a measurement for a custom needle.

Figure 16:
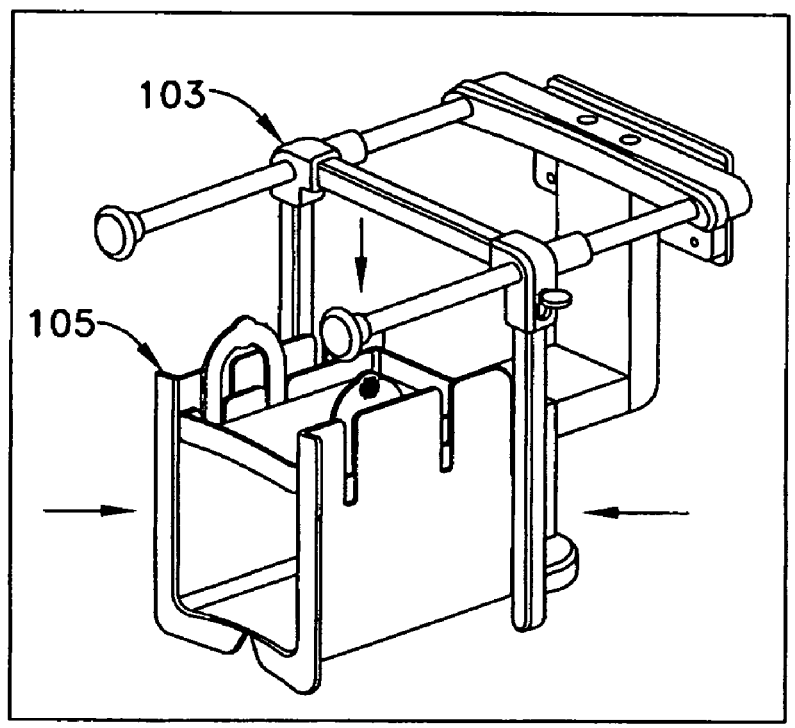
FIG. 16 is a view showing one embodiment of a step of determining a needle entry direction.

With reference to FIG. 16, the user inputs the needle entry direction, based on their judgment as to the appropriate entry direction. As shown in FIG. 16, the technician can choose from one of three entry directions—from top wall 147, from side wall 139, and from side wall 141.

Finally (although the order of input is not important), in a system where more than one size immobilization device may be used, an entry may be made to indicate which size unit is used.

Figure 12B:
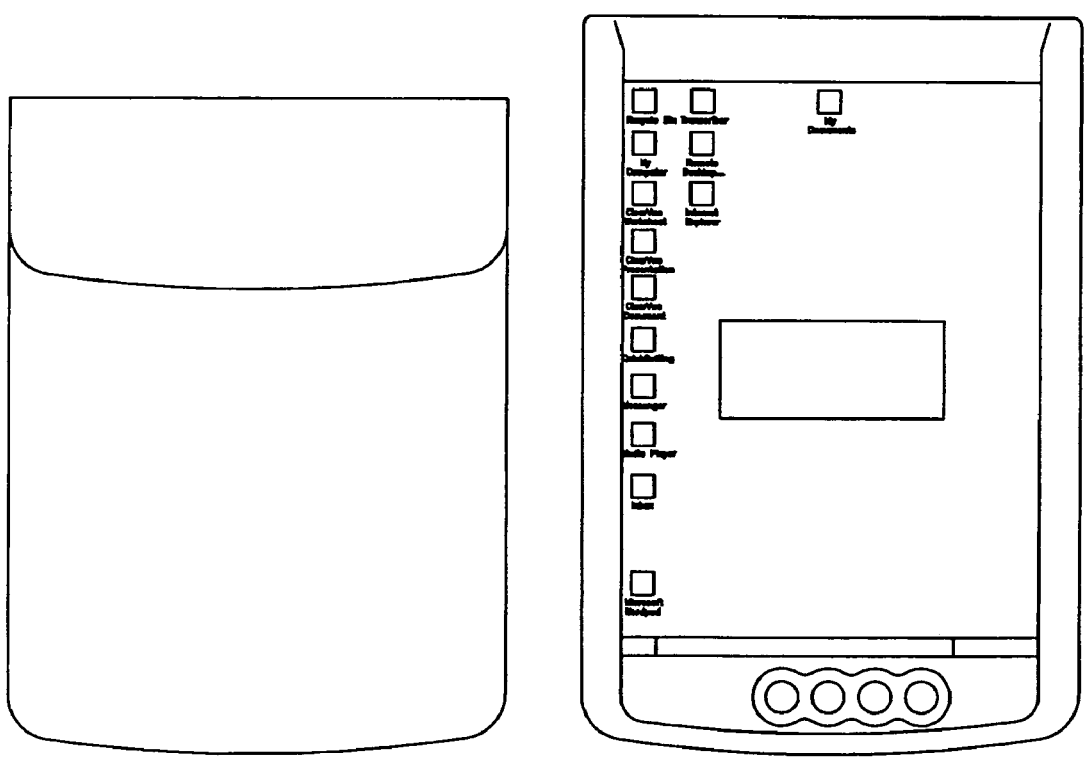
FIG. 12B is a view showing a PDA.

FIG. 12B illustrates a PDA of an embodiment of the present invention. A PDA may be used to receive the input of data read from the mammograms and any other data to be input (e.g., entry direction, needle length or immobilization device size) and output lesion location and/or settings for performing the procedure (such as where on the frame assembly to attach a needle assembly for performing needle localization).

Once this is done, the system has all of the data required to ascertain how to insert a needle with reference to an immobilization device to hit an area of interest identified on mammograms.

Figure 15:
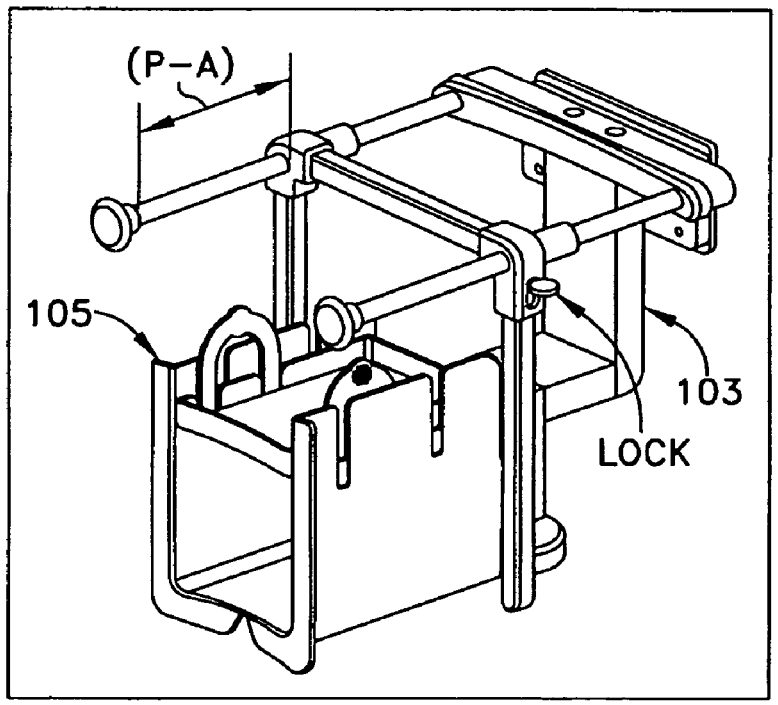
FIG. 15 is a view showing one embodiment of a step of determining a posterior-anterior distance of a needle from a reference point.

Consequently, at step 209, and with reference to FIG. 15, a first distance (e.g., a posterior-anterior distance (P-A)) is calculated and the corresponding setting on the marked indicia is output. The frame member portions 109a, 109b and 109c may then be positioned accordingly and locked in place using the locking tabs 129.

Figure 17:
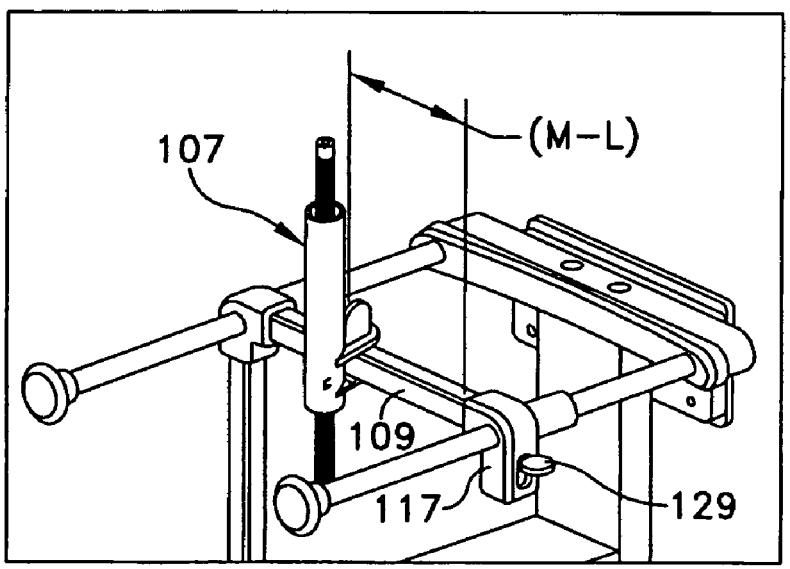
FIG. 17 is a view showing one embodiment of a step of determining a medio-lateral distance of a needle from a reference point.

In step 213, and with reference to FIG. 17, a second distance (e.g., a medio-lateral distance (M-L)) of the needle assembly 107 is set. This may specify the position that the needle assembly 107 should be attached to along the appropriate portion 109a, 109b or 109c. As shown in FIG. 17, the needle assembly 107 is attached to the frame member via the clamping assembly 171. The needle assembly 107 can be moved anywhere along the length of the frame member portions 109a, 109b or 109c.

Figure 18:
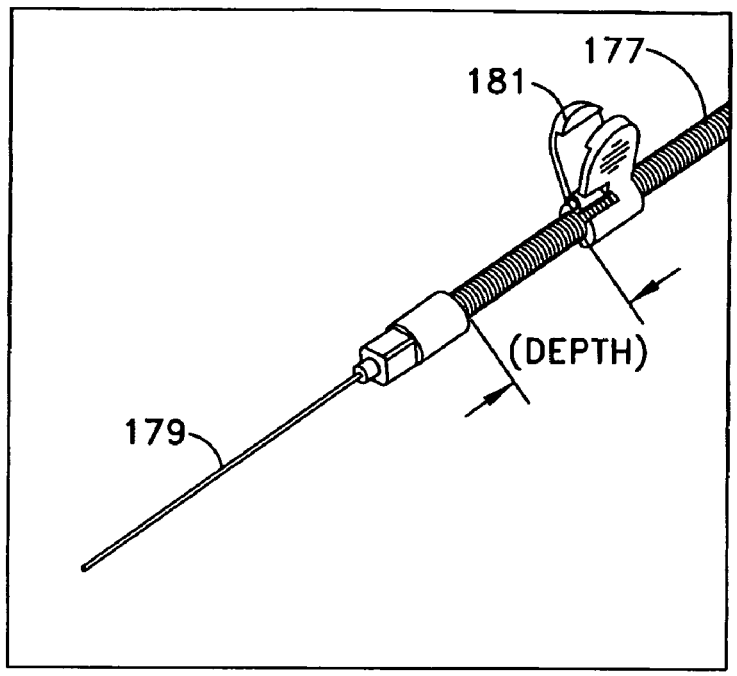
FIG. 18 is a view showing one embodiment of a step of determining a depth of needle penetration.

At step 215, and with reference to FIG. 18, the depth of the needle portion 179 penetration is set by selecting where the clamping assembly 171 should be attached to the tubular member 177 (with reference to the indicia on the tubular member) for insertion at the appropriate depth.

Figure 19:
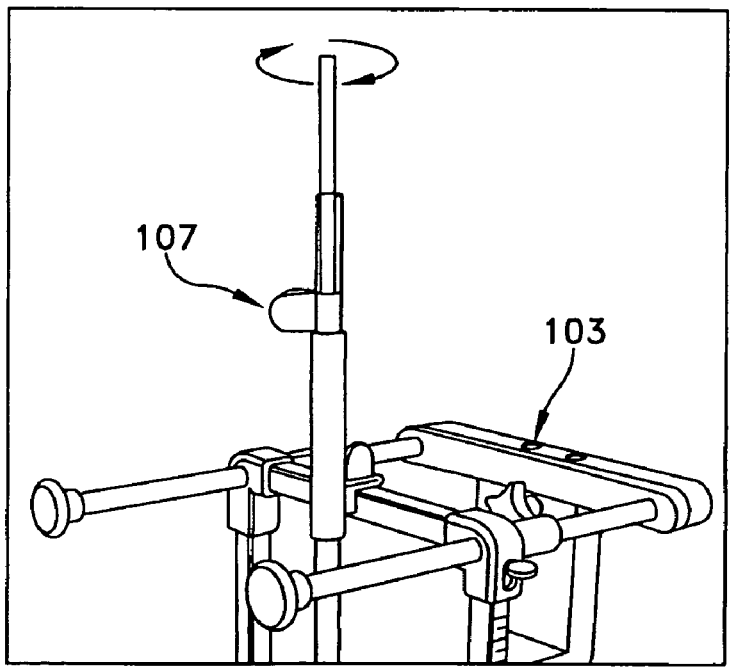
FIG. 19 is a view showing one embodiment of a step of inserting a needle to a correct depth.

At step 217, and with reference to FIG. 19, the needle portion 179 of the needle assembly 107 is then inserted or plunged to the correct depth. In this position, the medical procedure may be performed. Such medical procedures include needle localization, needle aspiration, vacuum-assisted biopsy, virtual guided breast surgery, in-office biopsy, sentinel node biopsy or therapeutic imaging correlation and implantation, for example.

Where needle localization is being performed, it may be desirable to remove the needle assembly in order to take a confirmatory mammogram. A formation may be included in the outer sleeve to permit a user to manually hold the needle in place while the needle is disconnected (e.g., unscrewed) from the tubular member. Once done, the remainder of the needle assembly may be removed and one or more confirmatory mammograms may be taken. The procedure may then be performed before or after removal of the immobilization device.

As one would appreciate based on this disclosure, various concepts described with reference to the embodiment of FIG. 1 may also be applied to the embodiment of FIG. 8. For example, historical reading may be taken to measure breast size or a pre-sterilized liner may be included.

In the embodiment of FIG. 8, the immobilization device provides relatively uniform compression around the entire breast, forming the breast into generally square-shape. Changing of breast shape is not preferred, however, during the procedure. In some embodiments, asymmetrical compression may be required.

Figure 20:
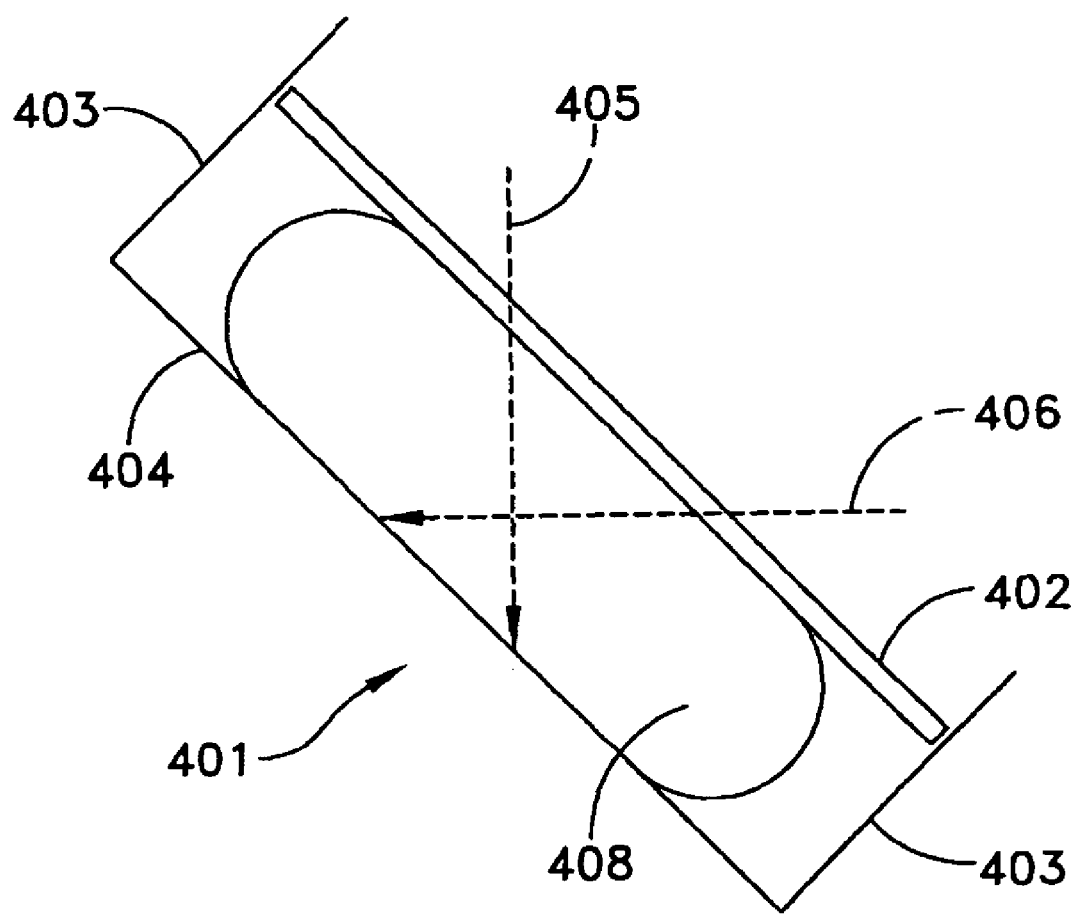
FIG. 20 is a schematic view of an immobilization assembly of another embodiment.

The embodiment of FIG. 20 illustrates an alternative immobilization device that may be used. In FIG. 20, the immobilization device 401 is not symmetric and the breast 408 is flattened when the top piece 402 is pushed down toward the bottom 404. A variable density filler, such as a radiolucent or translucent material or a radio-opaque material depending on the particular application, may be disposed below the bottom 404. This filler material may be manipulated to achieve a desired angle of image, e.g., a 45° offset. Sides 403 may be configured to be rounded at the corners. A first image may be taken from direction 405, and the width of the tissue being imaged is only square-root of two times the width of a flattened breast (where the device is at a 45° offset from the direction of orthogonal images). Similarly, a second image can be taken at a right angle and also have a similar width (e.g., along direction 406). This width may be less than the width of a uniformly compressed breast, however, and allow for lower radiation dosages in certain circumstances.

This design may be used with a flame as described above, suitably adapted for use with this immobilization device. The immobilization device 401 and frame (not shown) may be adapted so that needle insertion is from one location (orthogonal to the top 402) or from either of the same direction as the images are taken (e.g., along line 405 or 406) (or all of these).

It some circumstances, it can be preferable that the area of interest not be located near an edge of the breast; the width of the breast in the device is varied at the extreme edges and the image quality may be inferior for that reason. Also, there may be some movement of the breast at the very edges.

Where a screening mammogram is available, a user can assure that the area of interest is not near an edge by having the patient angle her body an appropriate amount so that the lesion is located more toward the center of the top 402 or bottom 404 of the immobilization unit 101.

In another embodiment, the edges of the breast may be compressed as well, with the compression not being uniform, causing the breast to assume a rectangular, pancake shape rather than a more squared shape as described with reference to FIG. 8.

In another embodiment, padding or some other soft material may be provided at the edges. This material may also be x-ray transparent.

As one would appreciate based on the disclosure provided herein, various alternatives described with respect to the previous embodiments may be applied to the embodiment of FIG. 20 as well, including use of a PDA or other device to calculate settings to insert a medical instrument to the appropriate location and providing the immobilization device and a medical instrument part (e.g., the parts of a needle assembly or all of a needle assembly except for the needle, where the needle assembly can be attached to one or more available, standard, pre-sterilized needles) in a pre-sterilized disposable package.

As can be appreciated by those skilled in the art, the apparatus and methods disclosed herein can be utilized for a variety of medical procedures. For example, the immobilization devices described herein can be employed in a sentinel node process in which a dye is injected into tissue surrounding a lymph node. This procedure may be referred to as nuclear localization. In addition, the apparatus may be used for antibody localization. The apparatus and methods may further be utilized in procedures requiring separate devices, such as a wheelchair or an operating table, for example, and the apparatus can be specifically tailored to accommodate such separate devices.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An immobilization device comprising:
a frame assembly;
a tissue immobilization assembly coupled to the frame assembly, the tissue immobilization assembly including a structure adapted to immobilize tissue; and
a needle assembly releasably connectable to the frame assembly, the needle assembly including a needle adapted to be inserted into the immobilized tissue,
wherein the structure of the immobilization assembly comprises a bottom wall and two side walls formed with the bottom wall, the bottom and side walls being sized to receive the tissue to be immobilized, and a top wall slidably connected to the side walls.

2. The immobilization device of claim 1, wherein the frame assembly includes a frame member constructed and arranged to mount the immobilization assembly thereon.

3. The immobilization device of claim 2, wherein the frame assembly further includes a seat configured to receive and secure the tissue immobilization assembly, the seat being adjustably secured to the frame member to adjust the position of the immobilization assembly with respect to the frame assembly.

4. The immobilization device of claim 3, wherein the frame assembly further includes at least one rod secured to the seat and adjustably secured to the frame member.

5. The immobilization device of claim 1, further comprising means for securing the top wall in place with respect to the side wall.

6. The immobilization device of claim 5, wherein the means for securing the top wall in place with respect to the side wall comprises a serrated area formed on the top wall adapted to mate with a serrated area formed on at least one of the side walls.

7. The immobilization device of claim 1, wherein each side wall has at least one slot formed therein, each slot being adapted to receive a positioning detent, which is formed along an edge of the top wall.

8. The immobilization device of claim 7, wherein the top wall is secured in place by at least one inverted U-shaped member, the at least one inverted U-shaped member being positioned adjacent a side wall and formed with the top wall.

9. The immobilization device of claim 8, wherein an outwardly facing surface of the at least one inverted U-shaped member has a serrated area adapted to mate with a serrated area formed on the respective inner facing surface of its respective side wall to secure the top wall in place with respect to the side wall.

10. The immobilization device of claim 1, wherein the needle assembly comprises a needle holder capable of being secured to the frame assembly.

11. The immobilization device of claim 10, wherein the needle holder includes an outer sleeve having a clamping assembly formed therewith adapted to be releasably clamped to the frame assembly.

12. The immobilization device of claim 11, wherein the needle holder further includes a tubular member and a needle portion adapted to be axially received within the outer sleeve.

13. The immobilization device of claim 12, wherein the outer sleeve of the needle holder is configured to enable the needle holder to be flexed apart to remove the needle holder from the tubular member and the needle portion without removing the needle portion from the tissue.

14. A kit for use in a medical procedure on tissue, the kit comprising:
  an immobilization assembly comprising a frame assembly including a structure adapted to immobilize tissue, the structure including a bottom wall and two side walls formed with the bottom wall, the bottom and side walls being sized to receive the tissue to be immobilized, and a top wall slidably connected to the side walls; and
  a needle assembly comprising a needle holder including an outer sleeve having a clamping assembly formed therewith adapted to be releasably clamped to the frame assembly of the immobilization assembly, and a tubular member and a needle portion adapted to be axially received within the outer sleeve,
  wherein the needle portion is configured to be inserted into the immobilized tissue.

* * * * *